United States Patent
Manuszak et al.

(10) Patent No.: US 12,385,103 B1
(45) Date of Patent: Aug. 12, 2025

(54) SURFACE PLASMON RESONANCE GENOTYPING FOR PLANT BREEDING

(71) Applicant: PIONEER HI-BRED INTERNATIONAL, INC., Johnston, IA (US)

(72) Inventors: Ryan Manuszak, Johnston, IA (US); Micheal Tuntland, Indianapolis, IN (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 427 days.

(21) Appl. No.: 17/573,230

(22) Filed: Jan. 11, 2022

Related U.S. Application Data

(60) Provisional application No. 63/137,769, filed on Jan. 15, 2021.

(51) Int. Cl.
 *C12Q 1/68* (2018.01)
 *C12Q 1/6806* (2018.01)
 *C12Q 1/6874* (2018.01)
 *C12Q 1/6895* (2018.01)

(52) U.S. Cl.
 CPC ......... *C12Q 1/6895* (2013.01); *C12Q 1/6806* (2013.01); *C12Q 1/6874* (2013.01); *C12Q 2600/13* (2013.01)

(58) Field of Classification Search
 None
 See application file for complete search history.

(56) References Cited

U.S. PATENT DOCUMENTS

2008/0131939 A1  6/2008  Roper

FOREIGN PATENT DOCUMENTS

| WO | WO/2003/100077 | 3/2004 |
|----|----------------|--------|
| WO | WO/2019/030383 | 2/2019 |

OTHER PUBLICATIONS

Ermini et al. (Anal Bioanal Chem., 404:985-993, Published 2013).*
Rasheed et al. (Molecular Plant, 19:1047-1064, Published Aug. 2017).*
Maniatis et al. (Molecular Cloning: A Laboratory Manual, Cold Spring Harbor Laboratory, 1982; see in particular pp. 387-389).*
Placido, A, et al. "A convenient renewable surface plasmon resonance chip for relative quantification of genetically modified soybean in food and feed." PloS one 15.2 (2020): e0229659.
Sipova and Jiri. "Surface plasmon resonance sensing of nucleic acids: A review." Analytica chimica acta 773 (2013): 9-23.
Mariani, S, et al. "Direct genotyping of C3435T single nucleotide polymorphism in unamplified human MDR1 gene using a surface plasmon resonance imaging DNA sensor." Analytical and Bioanalytical Chemistry 407.14 (2015): 4023-4028.

* cited by examiner

Primary Examiner — Vinod Kumar

(57) ABSTRACT

The present disclosure relates to compositions and methods for the use Surface Plasmon Resonance to genotype and sequence polynucleotides. Applications of these methods and compositions utilize Surface Plasmon Resonance for sequencing of a plant genome. Other applications include utilizing the sequence data for plant breeding.

19 Claims, 32 Drawing Sheets

Specification includes a Sequence Listing.

Fig. 2

(SEQ ID NO:1)          5'-Biotin-TEG- ATCT(C)TGCC-3'

(SEQ ID NO:2)                     3'-    TAGA(G)GACGG-5'

Fig. 4

```
SEQ ID NO:1     5'-Biotin- TEG -ATCT(C)CTGCC-3'
SEQ ID NO:3                3'-TAGA(C)GACGG-5'
```

Fig. 6

```
SEQ ID NO:1    5'-Biotin- TEG -ATCT(C)CTGCC-3'
SEQ ID NO:4              3'-TAGA(T)GACGG-5'
```

Fig. 8

(SEQ ID NO:1)   5'-Biotin-TEG -ATCT(C)CTGCC-3'
(SEQ ID NO:5)                3'-TAGA(A)GACGG-5'

Group 4
Short nonsense; Short probe; 1:1 binding

Fig. 10

SEQ ID NO:1    5'-Biotin- TEG -ATCT(C)CTGCC-3'
SEQ ID NO:6              3'-CAGT(A)CAGGT-5'

Fig. 12

```
SEQ ID NO:1    5'-Biotin- TEG -ATCT(C)CTGCC-3'
SEQ ID NO:8                3'-GTGGTAGA(G)GACGGGAAGATGCCTCATCAA-5'
```

Fig. 14

```
SEQ ID NO:1      5'-Biotin- TEG -ATCT(C)CTGCC-3'
SEQ ID NO:10              3'-GTGGTAGA(T)GACGGGAAGATGCCTCATCAA-5'
```

Fig. 16

```
SEQ ID NO:1     5'-Biotin- TEG -ATCT(C)CTGCC-3'
SEQ ID NO:11             3'-ATCGTACA(G)GTCTGGCACATACGTTAACGA-5'
```

Fig. 18

```
SEQ ID NO:7  5'-Biotin- TEG -CACCATCT(C)CTGCCCTTCTACGGAGTAGTT-3'
SEQ ID NO:8             3'-GTGGTAGA(G)GACGGGAAGATGCCTCATCAA-5'
```

Fig. 20

```
SEQ ID NO:7  5'-Biotin- TEG -CACCATCT(C)CTGCCCTTCTACGGAGTAGTT-3'
SEQ ID NO:9             3'-GTGGTAGA(C)GACGGGAAGATGCCTCATCAA-5'
```

Fig. 22

```
SEQ ID NO:7   5'-Biotin- TEG -CACCATCT(C)CTGCCCTTCTACGGAGTAGTT-3'
SEQ ID NO:10               3'-GTGGTAGA(T)GACGGGAAGATGCCTCATCAA-5'
```

Fig. 24

SEQ ID NO:7   5'-Biotin- TEG -CACCATCT(C)CTGCCCTTCTACGGAGTAGTT-3'
SEQ ID NO:11                3'-GTGGTAGA(A)GACGGGAAGATGCCTCATCAA-5'

Fig. 26

```
SEQ ID NO:7   5'-Biotin- TEG -CACCATCT(C)CTGCCCTTCTACGGAGTAGTT-3'
SEQ ID NO:12              3'-ATCGTACA(G)GTCTGGCACATACGTTAACGA-5'
```

Fig. 28

```
SEQ ID NO:7  5'-Biotin- TEG -CACCATCT(C)CTGCCCTTCTACGGAGTAGTT-3'
SEQ ID NO:2                         3'-TAGA(G)GACGG-5'
```

Fig. 30

```
SEQ ID NO:7  5'-Biotin- TEG -CACCATCT(C)CTGCCCTTCTACGGAGTAGTT-3'
SEQ ID NO:4                       3'-TAGA(T)GACGG-5'
```

Fig. 32

```
SEQ ID NO:7  5'-Biotin-TEG - CACCATCT(C)CTGCCCTTCTACGGAGTAGTT-3'
SEQ ID NO:6                            3'-CAGT(A)CAGGT-5'
```

SURFACE PLASMON RESONANCE GENOTYPING FOR PLANT BREEDING

CROSS-REFERENCE TO RELATED APPLICATIONS

This application is a continuation of U.S. Provisional Patent Application No. 63/137,769, filed on Jan. 15, 2021, the contents of which are incorporated by reference in their entirety into the present application.

REFERENCE TO A SEQUENCE LISTING

The official copy of the sequence listing is submitted electronically via EFS-Web as an ASCII formatted sequence listing with a file named "8539-US-PSP Sequence_ST25", having a size of 1.93 kilobytes and is filed concurrently with the specification. The sequence listing contained in this ASCII formatted document is part of the specification and is herein incorporated by reference in its entirety.

FIELD OF THE INVENTION

This disclosure is generally related to the field of molecular biology, and in particular embodiments, to the field of utilizing Surface Plasmon Resonance (SPR) for sequencing and genotyping polynucleotide sequences. In certain aspects, the sequencing and genotyping of polynucleotide sequences is applied for identifying polymorphisms within a genome. Further aspects include the use of SPR for high throughput sequencing of a genome. In other aspects, the sequencing and genotyping of polynucleotide sequences is applied for plant breeding. In aspects the disclosure relates to germplasm improvement. Accordingly, this disclosure provides compositions and methods for the identification, detection, and utilization of sequencing and genotyping a polynucleotide via SPR.

BACKGROUND

Traditional plant breeding strategies to develop new lines of plants that exhibit particular traits are time-consuming and costly. The use of assays to sequence and genotype polynucleotides within a genome are commonly applied for plant breeding. These types of assays deploy amplification through the Polymerase Chain Reaction (PCR) to ascertain the genetic sequences of the plant parents and subsequent progeny. Such assays allow for early detection and identification of progeny plants that contain the expected genetic background from the parents.

Surface Plasmon Resonance (SPR) is an optical biosensing technology that has be applied to quantitative and qualitative analysis in analytical chemistry, biochemistry, physics and engineering. The application of SPR utilizes polarized light that is directed through a prism towards a metal film and the resulting reflected light is collected and analyzed. The reflected light can be monitored for alterations or shifts in the reflectivity curve as assayed overtime. These alterations of shifts can assess the affinity of biomolecules in contact at the surface of the metal film. SPR technology has become an emerging technology in the field of direct real-time observation of biomolecular interactions. However, the use of this technology for genotyping and sequencing of polynucleotides for plant breeding has not been readily applied.

Accordingly, there is a need for methods to quickly and accurately sequence or genotype a polynucleotide sequence from a plant genome for the purpose of facilitating plant breeding activities such as line development, genetic mapping, quantitative trait loci mapping, fine mapping genes/traits, linkage disequilibrium mapping, marker-assisted back-crossing, genetic distance analysis, and discovery of markers linked to traits or phenotypes.

SUMMARY

Disclosed herein are sequences, constructs, and methods for genotyping a plant polynucleotide for the presence or absence of a Single Nucleotide Polymorphism (SNP) using a Surface Plasmon Resonance (SPR) assay. In some aspects the method comprises the aspect of providing an oligonucleotide probe. In other aspects the method comprises the aspect of providing a plant polynucleotide. In additional aspects the method comprises the aspect of hybridizing the oligonucleotide probe with the plant polynucleotide. In further aspects the method comprises the aspect of complexing the oligonucleotide probe and plant polynucleotide to an SPR biosensor chip. In other aspects the method comprises the aspect of quantitating the hybridization of the oligonucleotide probe with the plant polynucleotide to determine the affinity of oligonucleotide probe to the plant polynucleotide. In additional aspects the method comprises the aspect of determining that the plant polynucleotide contains the presence or absence of an SNP. In further aspects the method comprises the aspect of denaturing the oligonucleotide probe and plant polynucleotide to a single stranded oligonucleotide probe and a single stranded plant polynucleotide. In other aspects the method comprises the aspect of hybridizing the single stranded oligonucleotide probe with the single stranded plant polynucleotide. In additional aspects the method comprises the aspect of complexing the hybridized oligonucleotide probe and plant polynucleotide to an SPR biosensor chip. In additional aspects the method comprises the aspect of linking the hybridized oligonucleotide probe and plant polynucleotide to the surface of metal film on a glass chip and immobilizing the hybridized oligonucleotide probe and plant polynucleotide. In some aspects the method comprises the aspect of denaturing the oligonucleotide probe and plant polynucleotide to a single stranded oligonucleotide probe and a single stranded plant polynucleotide. In other aspects the method comprises the aspect of complexing the single stranded oligonucleotide probe to an SPR biosensor chip. In further aspects the method comprises the aspect of linking the single stranded oligonucleotide probe to the surface of metal film on a glass chip and immobilizing the single stranded oligonucleotide probe. In additional aspects the method comprises the aspect of hybridizing the single stranded oligonucleotide probe linked to the glass chip with the single stranded plant polynucleotide. In further aspects the method comprises the aspect of denaturing the oligonucleotide probe and plant polynucleotide to a single stranded oligonucleotide probe and a single stranded plant polynucleotide. In other aspects the method comprises the aspect of complexing the single stranded plant polynucleotide to an SPR biosensor chip. In some aspects the method comprises the aspect of linking the single stranded plant polynucleotide to the surface of metal film on a glass chip and immobilizing the single stranded plant polynucleotide. In further aspects the method comprises the aspect of hybridizing the single stranded plant polynucleotide linked to the glass chip with the single stranded oligonucleotide probe. In further aspects the disclosure provides for the metal to be copper, silver, aluminum or gold. In other aspects the probe comprises a plant genomic marker. Accordingly, the plant genomic marker may comprise an SNP. In additional aspects the plant polynucleotide comprises a plant genomic marker. Accordingly, the plant genomic marker may comprise an SNP. In some aspects the disclosure relates a plant polynucleotide selected from genomic DNA, cDNA, bacterial artificial chromosome, yeast artificial chromosome, whole-genome amplified DNA, and PCR product. In other aspects the plant polynucleotide is restricted with at least one restriction endonuclease. Accordingly the restriction endonuclease is a rare cutter or a frequent cutter. In some aspects the plant polynucleotide and the oligonucleotide probe share at least 90% sequence identity. In other aspects the SNP is either an A, C, T, or G. Furthermore the SNP is indicative of an economically important trait in a plant and wherein said economically important trait is selected from the group consisting of herbicide tolerance, disease resistance, insect or pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility. In other aspects the SNP is indicative of an insertion or deletion within a DNA sequence (INDEL), simple sequence repeats of DNA sequence (SSRs), a restriction fragment length polymorphism (RFLP), and a variation in copy number. In further aspects the SNP is indicative of a transgene. In further aspects the disclosure the genotyping is used for applications selected from the group consisting of genetic mapping, quantitative trait loci mapping, fine mapping genes/traits, linkage disequilibrium mapping, marker-assisted back-crossing, genetic distance analysis, discovery of markers linked to traits or phenotypes, and diagnostic genotyping of plant samples. In other aspects the disclosure related to producing multiple libraries from multiple plant polynucleotide samples and pooling the libraries prior to the SPR assay. As such, the multiple libraries may be obtained from at least two different plants. In other aspects the disclosure relates to identifying a plant that comprises the plant polynucleotide containing the presence or absence of an SNP and selecting the plant that comprises the plant polynucleotide containing the presence or absence of an SNP. In certain aspects the plant is selected from a forage crop, oilseed crop, grain crop, fruit crop, ornamental plants, vegetable crop, fiber crop, spice crop, nut crop, turf crop, sugar crop, beverage crop, tuber crop, root crop, and forest crop. For example the selected plant is a parent plant for a breeding population. Or, in other examples the selected plant is a progeny plant from a breeding population.

The subject disclosure relates to sequences, constructs, and methods for a plant selected with the presence or absence of a Single Nucleotide Polymorphism (SNP) using a Surface Plasmon Resonance (SPR) assay. In some aspects the plant is either a monocot plant or a dicot plant. For example the monocot plant is a corn plant. For example the dicot plant is a soybean plant.

The subject disclosure relates to sequences, constructs, and methods for determining a polynucleotide sequence in a sample using a Surface Plasmon Resonance (SPR) assay. In certain aspects the method comprises providing an oligonucleotide probe. In other aspects the method comprises providing a plant polynucleotide. In further aspects the method comprises hybridizing the oligonucleotide probe with the plant polynucleotide. In additional aspects the method comprises complexing the hybridized oligonucleotide probe and plant polynucleotide to an SPR biosensor chip. In other aspects the method comprises quantitating the hybridization of the oligonucleotide probe with the plant polynucleotide to determine the affinity of oligonucleotide probe to the plant polynucleotide. In additional aspects the method comprises determining that the plant polynucleotide contains the presence or absence of an SNP.

The subject disclosure relates to sequences, constructs, and methods for a high-throughput method for genotyping a genetic marker in a plurality of plant polynucleotides. In certain aspects the method comprises providing an oligonucleotide probe. In other aspects the method comprises providing a plurality of plant polynucleotide. In additional aspects the method comprises hybridizing the oligonucleotide probe with a plant polynucleotide. In further aspects the method comprises complexing the hybridized oligonucleotide probe and plant polynucleotide to an SPR biosensor chip. In other aspects the method comprises quantitating the hybridization of the oligonucleotide probe with the plant polynucleotide to determine the affinity of oligonucleotide probe to the plant polynucleotide. In some aspects the method comprises determining that the plant polynucleotide contains the presence or absence of an SNP.

The subject disclosure relates to sequences, constructs, and methods for identifying one or more Single Nucleotide Polymorphisms (SNP) in a plurality of polynucleotide sequences. In certain aspects the method comprises providing an oligonucleotide probe. In other aspects the method comprises providing a plurality of plant polynucleotide. In additional aspects the method comprises hybridizing the oligonucleotide probe with a plant polynucleotide. In further aspects the method comprises complexing the hybridized oligonucleotide probe and plant polynucleotide to an SPR biosensor chip. In other aspects the method comprises quantitating the hybridization of the oligonucleotide probe with the plant polynucleotide to determine the affinity of oligonucleotide probe to the plant polynucleotide. In some aspects the method comprises determining that the plant polynucleotide contains the presence or absence of an SNP.

The subject disclosure relates to sequences, constructs, and methods for identifying a phenotypic trait of interest in a plant. In certain aspects the method comprises providing an oligonucleotide probe. In other aspects the method comprises providing a plurality of plant polynucleotide. In additional aspects the method comprises hybridizing the oligonucleotide probe with a plant polynucleotide. In further aspects the method comprises complexing the hybridized oligonucleotide probe and plant polynucleotide to an SPR biosensor chip. In other aspects the method comprises quantitating the hybridization of the oligonucleotide probe with the plant polynucleotide to determine the affinity of oligonucleotide probe to the plant polynucleotide. In some aspects the method comprises determining that the plant polynucleotide contains the presence or absence of an SNP.

The subject disclosure relates to sequences, constructs, and methods for plant breeding by multiplex sample. In certain aspects the method comprises providing an oligonucleotide probe. In other aspects the method comprises providing a plurality of plant polynucleotide. In additional aspects the method comprises hybridizing the oligonucleotide probe with a plant polynucleotide. In further aspects the method comprises complexing the hybridized oligonucleotide probe and plant polynucleotide to an SPR biosensor chip. In other aspects the method comprises quantitating the hybridization of the oligonucleotide probe with the plant polynucleotide to determine the affinity of oligonucleotide probe to the plant polynucleotide. In some aspects the method comprises determining that the plant polynucleotide contains the presence or absence of an SNP.

The foregoing and other features will become more apparent from the following embodiments as provided in the Claims and Detailed Description, which proceeds with reference to the accompanying Sequence Listing.

SEQUENCE LISTING

The nucleic acid and amino acid sequences listed in the accompanying sequence listing are shown using standard letter abbreviations for nucleotide bases or amino acid residues, as defined in 37 C.F.R. § 1.822. Only one strand of each nucleic acid sequence is shown, but the complementary strand and reverse complementary strand are understood as included by any reference to the displayed strand. As the complement and the reverse complement of a primary nucleic acid sequence are necessarily disclosed by the primary sequence, the complementary sequence and reverse complementary sequence of a nucleic acid sequence are included by any reference to the nucleic acid sequence unless it is explicitly stated to be otherwise (or it is clear to be otherwise from the context in which the sequence appears).

BRIEF DESCRIPTION OF THE FIGURES

FIG. 2 provides an alignment of the short probe (SEQ ID NO:1)::short compliment (SEQ ID NO: 2).

FIG. 4 provides an alignment of the binding of the short probe (SEQ ID NO:1)::short MisC (SEQ ID NO:3).

FIG. 6 provides an alignment of the short probe (SEQ ID NO:1)::short MisT (SEQ ID NO: 4).

FIG. 8 provides an alignment of the short probe (SEQ ID NO:1)::short MisA (SEQ ID NO: 5).

FIG. 10 provides an alignment of the short probe (SEQ ID NO:1)::short nonsense (SEQ ID NO: 6).

FIG. 12 provides an alignment of the short probe (SEQ ID NO:1)::long compliment (SEQ ID NO: 8).

FIG. 14 provides an alignment of the short probe (SEQ ID NO:1)::long MisT (SEQ ID NO: 10).

FIG. 16 provides an alignment of the short probe (SEQ ID NO:1)::long nonsense (SEQ ID NO: 11).

FIG. 18 provides an alignment of the long probe (SEQ ID NO:7)::long compliment (SEQ ID NO: 8).

FIG. 20 provides an alignment of the long probe (SEQ ID NO:7)::long MisC (SEQ ID NO: 9).

FIG. 22 provides an alignment of the long probe (SEQ ID NO:7)::long MisT (SEQ ID NO: 10).

FIG. 24 provides an alignment of the long probe (SEQ ID NO:7)::long MisA (SEQ ID NO: 11).

FIG. 26 provides an alignment of the long probe (SEQ ID NO:7)::long nonsense (SEQ ID NO: 12).

FIG. 28 provides an alignment of the long probe (SEQ ID NO:7)::short compliment (SEQ ID NO: 2).

FIG. 30 provides an alignment of the long probe (SEQ ID NO:7)::short MisT (SEQ ID NO: 4).

FIG. 32 provides an alignment of the long probe (SEQ ID NO:7)::short nonsense (SEQ ID NO: 6).

DETAILED DESCRIPTION

Figure 1:
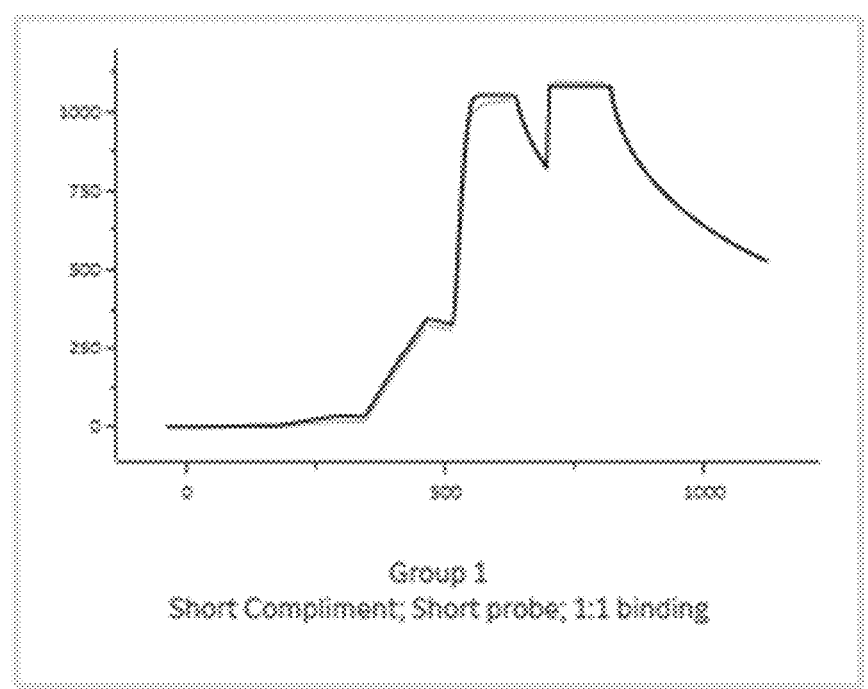
FIG. 1 provides the sensogram for the binding of the short probe (SEQ ID NO:1)::short compliment (SEQ ID NO:2).

Surface plasmon resonance (SPR) technology has been employed for quantitative and qualitative analysis in analytical chemistry, biochemistry, physics and engineering. SPR technology has become a leading technology in the field of direct real-time observation of biomolecular interactions. SPR technology is a powerful tool for studying biomolecule interactions. So far, in research settings, SPR based techniques have been used to investigate protein-peptide interactions, cellular ligation, protein-DNA interactions, and DNA hybridization. However, SPR based approaches have not yet been explored for plant breeding and plant genotyping.

Definitions

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

"Open reading frame" is abbreviated ORF.

As used herein, a "genomic region" is a segment of a chromosome in the genome of a cell that is present on either side of the target sequence or, alternatively, also comprises a portion of the target sequence. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases such that the genomic region has sufficient homology to undergo homologous recombination with the corresponding region of homology.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for the optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ a program of the LASERGENE bioinformatics computing suite (DNASTAR Inc., Madison, WI). Within the context of this application, it will be understood that where sequence analysis software is used for analysis, that the results of the analysis will be based on the "default values" of the program referenced unless otherwise specified. As used herein, "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ a program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5, and DIAGONALS SAVED=5. For nucleic acids, these parameters are KTUPLE=2, GAP PENALTY=5, WINDOW=4, and DIAGONALS SAVED=4. After alignment of the sequences using the Clustal V program, it is possible to obtain a "percent identity" by viewing the "sequence distances" Table in the same program. The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" Table in the same program. Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases. "BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence. It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any percentage from 50% to 100%. Indeed, any amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to the polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment. Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

A "centimorgan" (cM) or "map unit" is the distance between two polynucleotide sequences, linked genes, markers, target sequence, loci, or any pair thereof, wherein 1% of the products of meiosis are recombinant. Thus, a centimorgan is equivalent to a distance equal to a 1% average recombination frequency between the two linked genes, markers, target sequences, loci, or any pair thereof.

An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Optimally, an "isolated" polynucleotide is free of sequences (optimally protein-encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of a nucleotide sequence that naturally flank the polynucleotide in genomic DNA of the cell from which the polynucleotide is derived. Isolated polynucleotides may be purified from a cell in which they naturally occur. Conventional nucleic acid purification methods known to skilled artisans may be used to obtain isolated polynucleotides. The term also embraces recombinant polynucleotides and chemically synthesized polynucleotides.

The term "fragment" refers to a contiguous set of nucleotides or amino acids. In one embodiment, a fragment is 2, 3, 4, 5, 6, 7 8, 9, 10, 11, 12, 13, 14, 15, 16, 17, 18, 19, 20, or greater than 20 contiguous nucleotides. In one embodiment, a fragment is 2, 3, 4, 5, 6, 78, 9, 10, 11, 12, 13, 14, 15, 16, 17, 18, 19, 20, or greater than 20 contiguous amino acids. A fragment may or may not exhibit the function of a sequence sharing some percent identity over the length of the said fragment.

The terms "fragment that is functionally equivalent" and "functionally equivalent fragment" are used interchangeably herein. These terms refer to a portion or subsequence of an isolated nucleic acid fragment or polypeptide that displays the same activity or function as the longer sequence from which it derives. In one example, the fragment retains the ability to alter gene expression or produce a certain phenotype whether or not the fragment encodes an active protein. For example, the fragment can be used in the design of genes to produce the desired phenotype in a modified plant. Genes can be designed for use in expression by linking a nucleic acid fragment, whether or not it encodes an active enzyme, in the sense or antisense orientation relative to a plant promoter sequence.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in its natural endogenous location with its own regulatory sequences.

By the term "endogenous" it is meant a sequence or other molecule that naturally occurs in a cell or organism. In one aspect, an endogenous polynucleotide is normally found in the genome of a cell; that is, not heterologous.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a gene (referred to as the target gene), including a native gene, that was made by altering a target sequence within the target gene using any method known to one skilled in the art, including a method involving a guided Cas endonuclease system as disclosed herein.

The terms "knock-out", "gene knock-out," and "genetic knock-out" are used interchangeably herein. A knock-out represents a DNA sequence of a cell that has been rendered partially or completely inoperative by targeting with a Cas protein; for example, a DNA sequence prior to knock-out could have encoded an amino acid sequence or could have had a regulatory function (e.g., promoter).

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example, by homologous recombination (HR), wherein a suitable donor DNA polynucleotide is also used). Examples of knock-ins are a specific insertion of a heterologous amino acid coding sequence in a coding region of a gene or a specific insertion of a transcriptional regulatory element in a genetic locus.

As used herein, the term "InDel" is used generally to describe an insertion or a deletion in a gene. Thus, an "InDel" simply refers to a particular mutation that may be either an insertion, a deletion, or a combination thereof.

By "domain" it is meant a contiguous stretch of nucleotides (that can be RNA, DNA, and/or RNA-DNA-combination sequence) or amino acids.

The term "conserved domain" or "motif" means a set of polynucleotides or amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologs, they can be used as identifiers, or "signatures" to determine if a protein with a newly determined sequence belongs to a previously identified protein family.

A "codon-modified gene" or "codon-preferred gene" or "codon-optimized gene" is a gene having its frequency of codon usage designed to mimic the frequency of preferred codon usage of the host cell.

An "optimized" polynucleotide is a sequence that has been optimized for improved expression in a particular heterologous host cell.

A "plant-optimized nucleotide sequence" is a nucleotide sequence that has been optimized for expression in plants, particularly for increased expression in plants. A plant-optimized nucleotide sequence includes a codon-optimized gene. A plant-optimized nucleotide sequence can be synthesized by modifying a nucleotide sequence encoding a protein such using one or more plant-preferred codons for improved expression. See, for example, Campbell and Gowri (1990) *Plant Physiol.* 92:1-11 for a discussion of host-preferred codon usage.

As used herein, the term "copy number" refers to a sequence that is present at a different copy number in a locus of one chromosome relative to the same locus in a homologous chromosome. A copy number can be indicated by a sequence that is present in one chromosome but not the other (i.e., is bi-allelic), or by a sequence that is present with a copy number of one in one chromosome and a copy number of more than one (e.g., 2, 3 or 4 or more) in the homologous chromosome, for example. The term "copy number" includes in-dels of as small as a single nucleotide.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

As used herein, the term "oligonucleotide having a nucleotide sequence encoding a gene" means a nucleic acid sequence comprising the coding region of a gene, ie, a nucleic acid sequence encoding a gene product. The coding region can be present in either a cDNA, genomic DNA or RNA form. When present in DNA form, the oligonucleotide can be single-stranded (ie, the sense strand) or double-stranded.

As used herein, the term "probe" can hybridize to another oligonucleotide of interest, whether native to the purified restriction enzyme digestion product, generated by synthesis, recombination or PCR amplification, Refers to an oligonucleotide (ie, a sequence of nucleotides). The probe may be single stranded or double stranded. Probes are useful in the detection, identification and isolation of specific gene sequences. Any probe used in the present invention is labeled with any "reporter molecule", so it is not limited to enzymes (eg, ELISA, and enzyme-based histochemical assays), fluorescence, radioactivity, and luminescence systems. It is contemplated that detection is possible with any detection system, including these. It is not intended that the present invention be limited to any particular detection system or label.

As used herein, the term "transgene" means a nucleic acid sequence, which is partly or entirely heterologous, i.e., foreign, to the transgenic plant or cell into which it is introduced. A transgene can include one or more transcriptional regulatory sequences and any other nucleic acid, such as introns, that may be necessary for optimal expression of the selected nucleic acid, all operably linked to the selected nucleic acid, and may include an enhancer sequence.

The term "pooling", as used herein, refers to the grouping together or merging of samples for the purposes of maximizing advantage to the users. In particular the term "pooling" refers to the preparation of a collection of multiple samples to represent one sample of weighted value. Merging of multiple samples into one single sample is usually performed by mixing samples.

A "promoter" is a region of DNA involved in recognition and binding of RNA polymerase and other proteins to initiate transcription. The promoter sequence consists of proximal and more distal upstream elements; the latter elements often referred to as enhancers. An "enhancer" is a DNA sequence that can stimulate promoter activity. It may be an innate element of the promoter or a heterologous element inserted to enhance the level or tissue-specificity of a promoter. Promoters may be derived in their entirety from a native gene or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

Promoters that cause a gene to be expressed in most cell types at most times are commonly referred to as "constitutive promoters". The term "inducible promoter" refers to a promoter that selectively expresses a coding sequence or functional RNA in response to the presence of an endogenous or exogenous stimulus, for example by chemical compounds (chemical inducers) or in response to environmental, hormonal, chemical, and/or developmental signals.

Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability, or translation efficiency. Examples of translation leader sequences have been described (e.g., Turner and Foster, (1995) *Mol. Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or pre-mRNA. An RNA transcript is referred to as the mature RNA or mRNA when it is an RNA sequence derived from post-transcriptional processing of the primary transcript pre-mRNA. "Messenger RNA" or "mRNA" refers to the RNA that is without introns, and that can be translated into protein by the cell. "cDNA" refers to a DNA that is complementary to, and synthesized from, an mRNA template using the reverse enzyme transcriptase. The cDNA can be single-stranded or converted into a double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but has an effect on cellular processes. The terms "complement" and "reverse complement" are used interchangeably herein with respect to mRNA transcripts and are meant to define the antisense RNA of the message.

The term "genome" refers to the entire complement of genetic material (genes and non-coding sequences) that is present in each cell of an organism, or virus or organelle, and/or a complete set of chromosomes inherited as a (haploid) unit from one parent.

The term "operably linked" refers to the association of nucleic acid sequences on a single nucleic acid fragment so that the function of one is regulated by the other. For example, a promoter is operably linked with a coding sequence when it can regulate the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5,' and its complement is 3' to the target mRNA.

Generally, "host" refers to an organism or cell into which a heterologous component (polynucleotide, polypeptide, other molecules, cell) has been introduced. As used herein, a "host cell" refers to an in vivo or in vitro eukaryotic cell, prokaryotic cell (e.g., bacterial or archaeal cell), or cell from a multicellular organism (e.g., a cell line) cultured as a unicellular entity, into which a heterologous polynucleotide or polypeptide has been introduced. In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in an invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The term "recombinant" refers to an artificial combination of two otherwise separated segments of sequence, e.g., by chemical synthesis, or manipulation of isolated segments of nucleic acids by genetic engineering techniques.

The terms "plasmid," "vector" and "cassette" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in a linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector comprising a gene and having elements in addition to the gene that facilitates the transformation of a particular host cell. "Expression cassette" refers to a specific vector comprising a gene and having elements in addition to the gene that allows for the expression of that gene in a host.

The terms "recombinant DNA molecule", "recombinant DNA construct", "expression construct", "construct", and "recombinant construct" are used interchangeably herein. A recombinant DNA construct comprises an artificial combination of nucleic acid sequences, e.g., regulatory and coding sequences that are not all found together in nature. For example, a recombinant DNA construct may comprise regulatory sequences and coding sequences that are derived from different sources, or regulatory sequences and coding sequences derived from the same source but arranged in a manner different than that found in nature. Such a construct may be used by itself or may be used in conjunction with a vector. If a vector is used, then the choice of vector is dependent upon the method that will be used to introduce the vector into the host cells, as is well known to those skilled in the art. For example, a plasmid vector can be used. The skilled artisan is well aware of the genetic elements that must be present on the vector to transform, select and propagate host cells successfully. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened to obtain lines displaying the desired expression level and pattern. Such screening may be accomplished standard molecular biological, biochemical, and other assays including Southern analysis of DNA, Northern analysis of mRNA expression, PCR, real-time quantitative PCR (qPCR), reverse transcription PCR (RT-PCR), immunoblotting analysis of protein expression, enzyme or activity assays, and/or phenotypic analysis.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from *Zea mays* would be heterologous if inserted into the genome of an *Oryza sativa* plant, or of a different variety or cultivar of *Zea mays*; or a polynucleotide obtained from a bacterium was introduced into a cell of a plant), or sequence (e.g., a polynucleotide sequence obtained from *Zea mays*, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The term "expression", as used herein, refers to the production of a functional end-product (e.g., an mRNA, guide RNA, or a protein) in either precursor or mature form.

A "mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

The term "plant" generically includes whole plants, plant organs, plant tissues, seeds, plant cells, seeds and progeny of the same. The plant is a monocot or dicot. Plant cells include, without limitation, cells from seeds, suspension cultures, embryos, meristematic regions, callus tissue, leaves, roots, shoots, gametophytes, sporophytes, pollen and microspores. A "plant element" is intended to reference either a whole plant or a plant component, which may comprise differentiated and/or undifferentiated tissues, for example, but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue). It should be noted that a protoplast is not technically an "intact" plant cell (as naturally found with all components), as protoplasts lack a cell wall. The term "plant organ" refers to plant tissue or a group of tissues that constitute a morphologically and functionally distinct part of a plant. As used herein, a "plant element" is synonymous to a "portion" of a plant, and refers to any part of the plant, and can include distinct tissues and/or organs, and may be used interchangeably with the term "tissue" throughout. Similarly, a "plant reproductive element" is intended to generically reference any part of a plant that is able to initiate other plants via either sexual or asexual reproduction of that plant, for example, but not limited to: seed, seedling, root, shoot, cutting, scion, graft, stolon, bulb, tuber, corm, keiki, or bud. The plant element may be in plant or in a plant organ, tissue culture, or cell culture.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The term "monocotyledonous" or "monocot" refers to the subclass of angiosperm plants, also known as "monocotyledoneae", which seeds typically comprise only one embryonic leaf or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants, also known as "dicotyledoneae", whose seeds typically comprise two embryonic leaves or cotyledons. The term includes references to whole plants, plant elements, plant organs (e.g., leaves, stems, roots, etc.), seeds, plant cells, and progeny of the same.

As used herein, a "male-sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of the desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, the transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

The term "isoline" is a comparative term and references organisms that are genetically identical but differ in treatment. In one example, two genetically identical maize plant embryos may be separated into two different groups, one receiving a treatment (such as the introduction of a CRISPR-Cas effector endonuclease) and one control that does not receive such treatment. Any phenotypic differences between the two groups may thus be attributed solely to the treatment and not to any inherency of the plant's endogenous genetic makeup.

"Introducing" is intended to mean presenting to a target, such as a cell or an organism, a polynucleotide or polypeptide or polynucleotide-protein complex, in such a manner that the component(s) gains access to the interior of a cell of the organism or to the cell itself.

A "polynucleotide of interest" includes any nucleotide sequence encoding a protein or polypeptide that improves the desirability of crops, i.e., a trait of agronomic interest. Polynucleotides of interest include but are not limited to: polynucleotides encoding important traits for agronomics, insecticidal resistance, disease resistance, nematode resistance, herbicide resistance, microbial resistance, fungal resistance, viral resistance, fertility or sterility, grain characteristics, commercial products, phenotypic marker, or any other trait of agronomic or commercial importance. A polynucleotide of interest may additionally be utilized in either the sense or antisense orientation. Further, more than one polynucleotide of interest may be utilized together or "stacked" to provide additional benefit.

The compositions and methods herein may provide for an improved "trait" or "economic trait" or "trait of economic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

"Backcrossing" refers to the process used to introduce a nucleic acid sequence into plants. The backcrossing technique has been widely used for decades to introduce new traits into plants. Jensen, N., Ed. Plant Breeding Methodology, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

The term "complement" refers to a nucleotide sequence that is complementary to a given nucleotide sequence, i.e., the sequences are related by the base-pairing rules.

A "genetic map" is a description of genetic linkage relationships among loci on one or more chromosomes (or chromosomal) within a given species, generally depicted in a diagrammatic or tabular form. For each genetic map, distances between loci are measured by the recombination frequencies between them, and recombinations between loci can be detected using a variety of molecular genetic markers (also called "molecular markers," "genetic markers" or simply "markers"). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on the chromosome of interest, using a soybean reference genome, such as for example, Glyma1.1, which is publicly available on the SoyBase website. One of ordinary skill in the art can use a publicly available genome browser to determine the physical location of markers on a chromosome.

"Genetic recombination frequency" is the frequency of a crossing over event (recombination) between two genetic loci. Recombination frequency can be observed by following the segregation of markers and/or traits following meiosis.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

As used herein, the term "linkage" or "linked" is used to describe the degree with which one marker locus is associated with another marker locus or some other locus. The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" or ("LD") refers to a non-random segregation of genetic loci or traits for both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait. The degree of linkage of a molecular marker to a phenotypic trait is measured, e.g. as a statistical probability of co-segregation of that molecular marker with the phenotype.

Linkage disequilibrium is most commonly calculated using the formula described by Hill, W. G. and Robertson, A, Theor Appl. Genet 38:226-231 (1988). When r.sup.2=1, complete linkage disequilibrium exists between the two marker loci, meaning that the markers have not been separated by recombination and have the same allele frequency. Values for r.sup.2 above ⅓ indicate sufficiently strong LD to be useful for mapping (Ardlie at al., Nature Reviews Genetics 3:299-309 (2002)). Hence, alleles are in linkage disequilibrium when r.sup.2 values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

As used herein, the term "mapping population" may refer to a plant population used for gene mapping. Mapping populations are typically obtained from controlled crosses of parent genotypes. Decisions on the selection of parents and mating design for the development of a mapping population, and the type of markers used, depend upon the gene to be mapped, the availability of markers, and the molecular map. The parents of plants within a mapping population must have sufficient variation for the trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation.

The term "plant genomic marker" or "plant molecular marker" shall refer to any type of nucleic acid based marker, including but not limited to, Restriction Fragment Length Polymorphism (RFLP), Simple Sequence Repeat (SSR) Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

A "plant genomic marker" or "plant molecular marker" is a nucleotide sequence or encoded product thereof (e.g., a protein) used as a point of reference. For markers to be useful at detecting recombination, they need to detect differences, or polymorphisms, within the population being monitored. For molecular markers, this means differences at the DNA level due to polynucleotide sequence differences (e.g. SSRs, RFLPs, AFLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (or MAS) is a process by which phenotypes are selected based on marker genotypes.

"Marker assisted counter-selection" is a process by which marker genotypes are used to identify plants that will not be selected, allowing them to be removed from a breeding program or planting.

"Locus" and "marker locus" are used interchangeably herein and mean a position on a chromosome where a gene and/or marker is located.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

A "polymorphism" is a variation in the DNA that is too common to be due merely to a new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "non-significant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "single nucleotide polymorphism (SNP)" is a DNA sequence variation occurring when a single nucleotide—A, T, C or G—in the genome (or other shared sequence) differs between members of a biological species or paired chromosomes in an individual. For example, two sequenced DNA fragments from different individuals, AAGCCTA to AAGCTTA, contain a difference in a single nucleotide.

The terms "decreased," "fewer," "slower" and "increased" "faster" "enhanced" "greater" as used herein refers to a decrease or increase in a characteristic of the modified plant element or resulting plant compared to an unmodified plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400%) or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

As used herein, the term "before" in reference to a sequence position, refers to an occurrence of one sequence upstream, or 5', to another sequence.

The meaning of abbreviations is as follows: "sec" or "s" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" or "umole" mean micromole(s), "g" means gram(s), "μg" or "ug" means microgram(s), "ng" means nanogram(s), "U" means unit(s), "bp" means base pair(s) and "kb" means kilobase(s).

Unless defined otherwise, all technical and scientific terms used herein have the same meaning as commonly understood by one of ordinary skill in the art to which this disclosure relates. In case of conflict, the present application, including the definitions, will control. Unless otherwise required by context, singular terms shall include pluralities and plural terms shall include the singular. All publications, patents, and other references mentioned herein are incorporated by reference in their entireties for all purposes as if each publication or patent application were specifically and individually indicated to be incorporated by reference unless only specific sections of patents or patent publications are indicated to be incorporated by reference.

EMBODIMENTS

In an embodiment, the subject disclosure relates to compositions and methods for genotyping a plant polynucleotide using a Surface Plasmon Resonance (SPR) assay. In some aspects the SPR assay is a method for monitoring protein-nucleic acid interactions, and there exist protocols both for nucleic acid attachment as well as for analyzing the data. Illustrative references from the literature include Cho et al., "Binding Kinetics of DNA-Protein Interaction Using Surface Plasmon Resonance," Protocol Exchange, May 22, 2013; and Brockman et al., "A Multistep Chemical Modification Procedure To Create DNA Arrays on Gold Surfaces for the Study of Protein-DNA Interactions with Surface Plasmon Resonance Imaging," *Journal of the American Chemical Society* 121:8044-51 (1999), both of which are incorporated by reference herein in their entireties.

SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. The incident angle (or wavelength) at which the resonance occurs is highly dependent upon the refractive index in the immediate vicinity of the metal surface. Binding of biomolecules at the surface changes the local refractive index and results in a shift of the SPR minimum. By monitoring changes in the SPR signal, it is possible to measure binding activities at the surface in real time. Traditional SPR spectroscopy sensors, which measure the entire SPR curve as a function of angle or wavelength, have been widely used, but offer limited throughput. The high-throughput capability of a high-throughput SPR instrument is largely due to its imaging system. The development of SPR imaging allows for the simultaneous measurement of thousands of biomolecule interactions.

Typically, a SPR imaging apparatus consists of a coherent p-polarized light source expanded with a beam expander and consequently reflected from a SPR active medium to a detector. A CCD camera collects the reflected light intensity in an image. SPR imaging measurements are performed at a fixed angle of incidence that falls within a linear region of the SPR dip; changes in light intensity are proportional to the changes in the refractive index caused by binding of biomolecules to the surface. As a result, gray-level intensity correlates with the amount of material bound to the sensing region. In addition, one of the factors determining the sensitivity of a SPR imaging system is the intensity of the light source. The signal strength from the metal surface is linearly proportional to the incoming light strength, so a laser light source is preferred over light-emitting diode and halogen lamps.

The SPR instrument is an optical biosensor that measures binding events of biomolecules at a metal surface by detecting changes in the local refractive index. The depth probed at the metal-aqueous interface is typically 200 nm, making SPR a surface-sensitive technique ideal for studying interactions between immobilized biomolecules and a solution-phase analyte. SPR technology offers several advantages over conventional techniques, such as fluorescence or ELISA (enzyme-linked immunosorbent assay) based approaches. First, because SPR measurements are based on refractive index changes, detection of an analyte is label free and direct. The analyte does not require any special characteristics or labels (radioactive or fluorescent) and can be detected directly, without the need for multistep detection protocols. Secondly, the measurements can be performed in real time, allowing the user to collect kinetic data, as well as thermodynamic data. Lastly, SPR is a versatile technique, capable of detecting analytes over a wide range of molecular weights and binding affinities.

SPR may be sustained in planar surfaces. A number of commercial instruments based on the Kretschmann configuration (e.g., Biacore, Uppsala, Sweden) and SPR imaging (e.g., GWC Technologies; Madison, Wis.; or Horiba; Kyoto, Japan) are available and have well established protocols for attaching DNA to their surfaces, as single spots and in multiplexed array patterns. In the Kretschmann configuration, a metal film, typically gold, is evaporated onto the side of a prism and incident radiation is launched at an angle to excite the surface plasmons. An evanescent wave penetrates through the metal film exciting plasmons on the other side, where it may be used to monitor near-surface and surface interactions near the gold film. At the resonant angle, the light reflected from the prism-gold interface is severely attenuated. Assuming fixed wavelength illumination, binding interactions may be examined by monitoring both the intensity of the reflected light at a fixed angle close to the resonant angle, as well as by monitoring the changes in angle of incidence required to establish surface plasmon resonance conditions (minimum reflectivity). When a 2D imaging device such as a CCD or CMOS camera is utilized to monitor the reflected light, the entire illumination area may be imaged with high resolution. This method is called surface plasmon resonance imaging (SPRi). It allows high throughput analysis of independent regions on the surface simultaneously. Broadband illumination may also be used, in a fixed angle configuration, wherein the wavelength that is coupled to the SPR is identified spectroscopically by looking for dips in the reflected spectrum. Surface interactions are monitored through shifts in the resonant wavelength.

In some aspects the subject disclosure relates to a sensogram that is produced from the binding of the plant polynucleotide and the oligonucleotide probe. The sensogram depicts the affinity of the plant polynucleotide and the oligonucleotide probe. In some aspects the plant polynucleotide will bind to the oligonucleotide probe. In other aspects the plant polynucleotide binds to the oligonucleotide probe via hydrogen bonding. In some aspects the plant polynucleotide binds to the oligonucleotide probe with 80%, 81%, 82%, 83%, 84%, 85%, 86%, 87%, 88%, 89%, 90%, 91%, 92%, 93%, 94%, 95%, 96%, 97%, 98%, 99%, or 100% sequence identity. Those with skill in the art will appreciate that the affinity of the plant polynucleotide will bind to the oligonucleotide probe will be quantitated in a unique manner that is readily detectable and reproduceable.

In other aspects the subject disclosure relates to an SPR biosensor chip. In further aspects the SPR biosensor chip may be a metal film on a glass chip. In other aspects the metal of the SPR biosensor chip may be copper, aluminum, steel, lead, silver, gold, titanium, tin, or bronze. In further aspects the SPR biosensor chip may be a polystyrene bead. For example, the SPR biosensor chip may be a carboxymethylated dextran biosensor chip. In further aspects the SPR biosensor chip is complexed with a polynucleotide. For example the SPR biosensor chip is complexed with a plant polynucleotide. In another example the SPR biosensor chip is complexed with an oligonucleotide probe. In other aspects the SPR biosensor chip is complexed with a single stranded polynucleotide. For example the SPR biosensor chip is complexed with a single stranded plant polynucleotide. In another example the SPR biosensor chip is complexed with an single stranded oligonucleotide probe. In additional aspects the SPR biosensor chip is complexed with a polynucleotide comprising a first polynucleotide hybridized to a second polynucleotide. For example the single stranded oligonucleotide probe is hybridized to the single stranded plant polynucleotide and then complexed to the SPR biosensor chip. In an aspect, the polynucleotides are bound to the SPR biosensor chip. In specific aspects the polynucleotides are bound to the SPR biosensor chip via a covalent bond, a non-covalent bond, a hydrogen bond, an amine bond, a streptavidin bond, or an amide bond.

In other aspects the subject disclosure relates to genotyping. In certain aspects the genotyping is used for applications selected from the group consisting of genetic mapping, quantitative trait loci mapping, fine mapping genes/traits, linkage disequilibrium mapping, marker-assisted back-crossing, genetic distance analysis, discovery of markers linked to traits or phenotypes, and diagnostic genotyping of plant samples. Those with skill in the art will appreciate that specific genetic loci or traits correlating with particular phenotypes can be mapped within the plant genome. The plant breeder can advantageously use plant genomic markers to identify desired individual plants by detecting plant genomic markers (for example, marker alleles) that show a statistically significant probability of co-segregation with a desired phenotype, manifested as linkage disequilibrium. By identifying a plant genomic marker or clusters of plant genomic markers that co-segregate with an economically important trait (e.g., a trait of interest), the breeder is able to rapidly select a desired phenotype by selecting for the proper molecular marker plant genomic marker (a process called marker-assisted selection, or "MAS").

A variety of methods well known in the art are available for detecting molecular markers or clusters of molecular markers that co-segregate with a trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, plant lines are obtained from pre-existing populations with multiple founders, e.g. elite breeding lines. Population-based association analyses rely on the decay of linkage disequilibrium (LD) and the idea that in an unstructured population, only correlations between genes controlling a trait and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the dose proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait at that position on the genetic map (which will fall between two particular marker loci).

In certain aspects plant genomic markers are identified using the SPR methods disclosed herein. The SPR methods involve detecting the presence of at least one marker allele associated with the phenotype of interest within a plant. In specific aspects the SPR methods are used for population-based association analysis. In other aspects the SPR methods are used for traditional linkage analysis.

A common measure of linkage is the frequency with which traits cosegregate. This can be expressed as a percentage of cosegregation (recombination frequency) or in centiMorgans (CM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation. The subject disclosure relates to compositions and methods for the use of SPR to detect much marker loci associated with traits and the segregation of the loci from the traits during plant breeding.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25%, or less) are said to be "proximal to" each other.

Although particular marker alleles can show co-segregation with a phenotypic trait it is important to note that the marker locus is not necessarily responsible for the expression of the phenotypic trait. For example, it is not a requirement that the marker polynucleotide sequence be part of a gene that imparts the phenotypic trait (for example, be part of the gene open reading frame). The association between a specific marker allele and the phenotypic trait is due to the original "coupling" linkage phase between the marker allele and the allele in the ancestral plant line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

A marker of the subject disclosure can also be a combination of alleles at marker loci, otherwise known as a haplotype. The skilled artisan would expect that there might be additional polymorphic sites at marker loci in and around the chromosome markers, wherein one, or more polymorphic sites is in linkage disequilibrium (LD) with an allele associated with phenotypic trait. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection is a further aspect of the subject disclosure. Molecular markers can be used in a variety of plant breeding applications (e.g. see Staub et al. (1996) Hortscience 729-741; Tanksley (1983) Plant Molecular Biology Reporter 1:3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. seed characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42:1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints (Young et al, (1998) Genetics 120:579-585). In classical breeding it is usually only by chance that recombinations are selected that contribute to a reduction in the size of the donor segment (Tanksley et al. (1989). Biotechnology 7:257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with, markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are (i) defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as RFLPs, can be used in marker assisted selection protocols.

SSRs can be defined as relatively short runs of tandemly repeated DNA with lengths of 6 bp or less (Tautz (1989) Nucleic Acid Research 17:6463-6471; Wang et al. (1994) Theoretical and Applied Genetics, 88:1-6) Polymorphisms arise due to variation in the number of repeat units, probably caused by slippage during DNA replication (Levinson and Gutman (1987) Mol Biol Evol 4:203-221). The variation in repeat length may be detected by designing PCR primers to the conserved non-repetitive flanking regions (Weber and May (1989) Am J Hum Genet. 44:388-396), SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from plant lines can be obtained by gel electrophoresis of the amplification products. Scoring of marker genotype is based on the size of the amplified fragment. An SSR service for soybean is available to the public on a contractual basis by DNA Landmarks in Saint-Jean-sur-Richelieu, Quebec, Canada.

Various types of RFLP markers can also be generated. Most commonly, amplification primers are used to generate fragment length polymorphisms. Such RFLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in soybean (Bhattramakki et al. (2002). Plant Mol Biol 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™. (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased PRSR resistance, but the allele 'T' might also occur in the plant breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Methods of using plant genomic markers that are linked to a phenotypic trait may result in a cost savings for plant developers, because such methods may eliminate the need to cross plants and then phenotype the progenies of the cross. In some embodiments, plant genomic markers flanking the phenotypic trait may be used to transfer segment(s) of donor parent DNA that unequivocally contain phenotypic trait. In some embodiments, a method for using plant genomic markers flanking the phenotypic trait to transfer segment(s) of donor parent DNA that unequivocally contain the phenotypic trait may comprise analyzing the genomic DNA of two parent plants with probes that are specifically hybridizable to markers linked to the phenotypic trait; sexually crossing the two parental plant genotypes to obtain a progeny population, and analyzing those progeny for the presence of the markers linked to the phenotypic trait; backcrossing the progeny that contain the markers linked to the phenotypic trait to the recipient genotype to produce a first backcross population, and then continuing with a backcrossing program until a final progeny is obtained that comprises any desired trait(s) exhibited by the parent genotype and the phenotypic trait. In particular embodiments, individual progeny obtained in each crossing and backcrossing step are selected by SNP marker analysis of the subject disclosure at each generation. In some embodiments, analysis of the genomic DNA of the two parent plants with probes that are specifically hybridizable to markers to the phenotypic trait reveals that one of the parent plants comprises fewer of the linked markers to which the probes specifically hybridize, or none of the linked markers to which the probes specifically hybridize.

In some aspects the compositions and methods of the subject disclosure relate to the use of SPR to detect an insertion or deletion within a DNA sequence (INDEL), simple sequence repeats of DNA sequence (SSRs), a restriction fragment length polymorphism (RFLP), or a variation in copy number within plant genomic DNA. In some aspects, plant genomic markers that are linked or that reside within the phenotypic trait may be used to introduce the phenotypic trait into a plant by genetic transformation. In other aspects, a method for introducing the phenotypic trait into a plant by genetic recombination may comprise analyzing the genomic DNA of a plant with probes that are specifically hybridizable to markers linked to phenotypic trait in the plant; isolating a segment of the genomic DNA of the plant comprising phenotypic trait, for example, by extracting the genomic DNA and digesting the genomic DNA with one or more restriction endonuclease enzymes; optionally amplifying the isolated segment of DNA; introducing the isolated segment of DNA into a cell or tissue of a host plant; and analyzing the DNA of the host plant with probes that are specifically hybridizable to markers linked to the phenotypic trait to identify the phenotypic trait in the host plant. In particular embodiments, the isolated segment of DNA may be introduced into the host plant such that it is stably integrated into the genome of the host plant.

In some aspects the compositions and methods of the subject disclosure relate to the use of SPR to determining a polynucleotide sequence in a sample. In aspects of this method, the sample is a polynucleotide or an oligonucleotide. In further aspects, the sample is obtained from plant polynucleotides (genomic DNA, mitochondrial DNA, or chloroplast DNA). In further aspects the compositions and methods of the subject disclosure relate to the use of SPR to a method for identifying one or more Single Nucleotide Polymorphisms (SNP) in a plurality of polynucleotide sequences. In other aspects the compositions and methods of the subject disclosure relate to the use of SPR as a high-throughput method for genotyping a genetic marker in a plurality of plant polynucleotides. Accordingly, a plurality of plant polynucleotides may be obtained from two, three, four, five, six or more individual plants. In some aspects the plants are of the same genus. In other aspects the plants are of different genus. In additional aspects the plants are of the same variety. In other aspects, the plurality of plant polynucleotices is assayed in a single reaction. Such an assay is said to be a multiplex. In further aspects the compositions and methods of the subject disclosure relate to the use of SPR to a method of plant breeding by multiplex sample. In further aspects the compositions and methods of the subject disclosure relate to the use of SPR to a method of identifying a phenotypic trait of interest in a plant.

In some aspects, plants are subjected to a genotype and/or zygosity determination. Once plants have been genotyped, and/or their zygosity determined, the skilled artisan may select those plants that have a desired genetic composition. Such selected plants may be used in further crosses, selfing, or cultivation. Methods of introgression of a trait that are directed according to methods of the disclosure reduce or eliminate the cultivation and/or reproduction of plants that do not have a desired genetic composition, and thereby provide desirable reliability and predictability (through expected Mendelian patterns of inheritance). In further aspects the compositions and methods of the subject disclosure relate to the use of SPR to a method for determining the zygosity of a plant.

In further aspects the compositions and methods of the subject disclosure relate to the use of SPR to detect plant genomic markers that are linked to or that reside within the phenotypic trait. Accordingly, the compositions and methods of the subject disclosure may be used to introduce the phenotypic trait into other organisms, for example, plants. In some aspects, plant genomic markers that are linked to or that reside within the phenotypic trait may be used to produce hybrid seed. The production of hybrid seed according to such methods may result in a cost savings due to elimination of hand or mechanical detasseling, and may further increase seed yield.

In some aspect, the subject disclosure relates to assaying a plant genomic marker. The plant genomic marker is assayed as a polynucleotide sequence. Accordingly, in certain aspects the plant genomic marker is selected from the group consisting of genomic DNA, cDNA, bacterial artificial chromosome, yeast artificial chromosome, whole-genome amplified DNA, and PCR product. The polynucleotide sequence to be assayed may be obtained or stored in these forms and utilized in the compositions and assays of the subject disclosure. In other aspect the plant genomic markers are produced in a library of a polynucleotide sequence. The library may be a single specific library or as multiple libraries. In other aspects, the polynucleotide sequences being assayed via the SPR methods to detect and identify plant genomic markers may be whole genomic sequences.

In some aspects the polynucleotide sequences being assayed via the SPR methods to detect and identify plant genomic markers may be fragmented genomic sequences. In some aspects the polynucleotide sequence may be fragmented by a restriction endonuclease. In other aspects the restriction endonuclease may be a rare cutter. In other aspects the restriction endonuclease may be a frequent cutter. Those with skill in the art will appreciate which restriction endonucleases are considered rare and frequent cutters.

In some aspect, the subject disclosure relates to identification and detection of an economically important trait in a plant. In further aspects the economically important trait is selected from the group consisting of herbicide tolerance, disease resistance, insect or pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility.

In other aspects, the subject disclosure relates to identification and detection of native and transgenic traits. Native traits of interest may be detected with the SPR assay of the subject disclosure. Exemplary native traits of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers.

Transgenes of interest may be detected with the SPR assay of the subject disclosure. Exemplary transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers.

1. Insect Resistance

Various insect resistance genes can be further analyzed with the SPR assay to detect an insect resistance gene. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab (truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A (a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be can be further analyzed with the SPR assay to detect a herbicide tolerance gene. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, MEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83), the *B. subtilis* PPO gene (Li, X. and Nicholl D. 2005. Development of PPO inhibitor-resistant cultures and crops. *Pest Manag. Sci.* 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), Is genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be further analyzed with the SPR assay to detect an agronomic trait gene. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native ace synthase gene, resulting in reduced ethylene production and delayed fruit ripening. Whereas, the aced genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by espB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be can be further analyzed with the SPR assay to detect a DNA binding gene. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be can be further analyzed with the SPR assay to detect a small RNA sequence. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be can be further analyzed with the SPR assay to detect a reporter gene. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), 8-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Some aspects of the of the present disclosure include plants in which the subject compositions and methods are deployed. In some aspects the plants are assayed using the SPR methods of the subject disclosure. In other aspects the SPR methods of the subject disclosure are used to identify and select a plant of interest that contains a plant molecular marker identified via the SPR method. In further aspects the plant of interest may be a parent plant. In some aspects the plant of interest may be a progeny plant. By way of non-limiting example, a plant assayed using the SPR method of the subject disclosure may be a plant of agronomic value, for example and without limitation: maize; soybean; alfalfa; wheat; rapeseed; rice; sorghum; beet; Brachypodium; monocots; dicots; various vegetables including cucumber, tomato, peppers, etc.; various trees including apple, pear, peach, cherry, redwood, pine, oak, etc.; and various ornamental plants. By way of non-limiting example, a plant assayed using the SPR method of the subject disclosure may be a plant selected from the group consisting of a forage crop, oilseed crop, grain crop, fruit crop, ornamental plants, vegetable crop, fiber crop, spice crop, nut crop, turf crop, sugar crop, beverage crop, tuber crop, root crop, and forest crop. In other aspects the plant may be a monocot plant. In further aspect the plant may be a dicot plant.

In other aspects, the subject disclosure provides a seed cell, tissue, or plant obtained from the SPR method of the subject disclosure. In subsequent aspects a seed may be composed of three structural parts: (1) the outer hull, which is a protective outer covering; and (2) the embryo (which also includes the cotyledons). The subject disclosure also relates to one or more plant parts. In an aspect, the plant parts include plant cells, plant protoplasts, plant cell tissue cultures from which plants can be regenerated, plant DNA, plant calli, plant clumps, and plant cells that are intact in plants or parts of plants, such as embryos, pollen, ovules, flowers, seeds, leaves, roots, root tips, anthers, and the like.

In particular aspects, the plant may be a sexually-reproducing plant. In an aspect the subject disclosure provides a method for producing a plant using the SPR methods, the method comprising the steps of: a) crossing a female parent plant with a male parent plant; b) harvesting a progeny seed from the cross of (a); c) planting the progeny seed; and, d) growing the progeny seed, wherein the progeny seed comprises a plant molecular marker that is identified via an SPR method. In additional aspects, the subject disclosure relates to female and male parent plants that are plants. In further aspects the male parent plant is isogenic to the female parent plant. In an aspect of the embodiment, the male parent plant is homozygous or heterozygous for the plant molecular marker. In another aspect of the embodiment, the female parent plant is homozygous or heterozygous for plant molecular marker. In other aspects the SPR method of the subject disclosure is used to identify the homozygous or heterozygous plant molecular marker.

In yet another aspect of the subject disclosure, processes are provided for producing progeny plants, which processes generally comprise crossing a first parent plant with a second parent plant wherein at least one of the first parent plant or the second parent plant. These processes may be further exemplified as processes for producing progeny seed or plants, wherein a first plant is crossed with a second plant. In other aspects, the progeny plants may be identified and selected to contain a plant molecular marker, wherein the plant molecular marker is assayed using the SPR method of the subject disclosure.

Any time the male plant is crossed with another, different inbred plant, a progeny or first generation ($F_1$) hybrid plant is produced. As such, a progeny or $F_1$ hybrid plant may be produced by crossing the first plant with any second inbred plant. Therefore, any progeny or $F_1$ hybrid plant or seed that comprises a plant molecular marker which is produced with the first parent plant as a parent is an embodiment of the subject disclosure.

In embodiments of the present disclosure, the step of "crossing" the plant comprises planting, preferably in pollinating proximity, seeds of a first inbred plant and a second, distinct inbred plant. In other embodiments, the step of "crossing" the plant comprises planting, manually pollinating a first inbred plant with pollen to a second, distinct inbred plant.

A further step comprises harvesting the seeds, near or at maturity, from the plant that received the pollen. In a particular aspect, seed is harvested from the female parent plant, and when desired, the harvested seed can be grown to produce a progeny or first generation ($F_1$) hybrid plant.

Yet another step comprises drying and conditioning the seeds, including the treating, sizing (or grading) of seeds, and packaging for sale to growers for the production of oil and grain. As with inbred seed, it may be desirable to treat hybrid seeds with compositions that render the seeds and seedlings grown therefrom more hardy when exposed to adverse conditions. Mention should be made that resulting progeny or hybrid seed may be sold to growers for the production of oil and grain and not for breeding or seed production.

Still further, the subject disclosure provides a progeny plant produced by growing the harvested seeds produced on the plant that comprises the plant molecular maker as well as grain produced by the progeny plant. In some aspects, the SPR methods of the subject disclosure are used to identify and obtain the progeny plants containing a plant molecular marker.

In an additional embodiment, the subject disclosure relates to a method for producing a progeny plant, the method further comprising the steps of: e) crossing the progeny plant, with another plant comprising a desired trait to produce F1 progeny plants; f) selecting F1 progeny plants that have the desired trait to produce selected F1 progeny plants; g) crossing the selected F1 progeny plants with the progeny plant that comprises the plant molecular marker to produce backcross progeny plants; h) selecting for backcross progeny plants that have the desired trait; and, i) repeating steps (g) and (h) three or more times in succession to produce selected fourth or higher backcross progeny plants that comprise the desired trait. In some aspects, the SPR methods of the subject disclosure are used to identify and obtain the progeny plants containing a plant molecular marker.

All references, including publications, patents, and patent applications, cited herein are hereby incorporated by reference to the extent they are not inconsistent with the explicit details of this disclosure and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

Embodiments and aspects of the subject disclosure are further exemplified in the following Examples. It should be understood that these examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Identification of Single Nucleotide Polymorphisms (SNPs) from Plant Polynucleotides The following polynucleotide fragments were identified from plant genomes and oligonucleotides comprising these plant genomic polynucleotides were synthesized. The *Zea mays* genomic database was analyzed to identify a marker that contains SNPs within the polynucleotide sequence. The MZA11874-27-Q1 SNP was identified and varying oligonucleotide sequences containing unique SNPs were synthesized. Table 1 lists the oligonucleotide sequences that were identified and synthesized. The SNPs are identified within parenthesis.

These oligonucleotides were aliquoted into a 200 uM stock solution using ultra-pure DNAse/RNAse free water (Table 2).

TABLE 2

| ID | MW (g/mol) | g | mol | ml to add for 200 μM |
|---|---|---|---|---|
| Capture probe long | 9550.5 | 0.00116 | 1.21E−07 | 0.607 |
| Long nonsense | 9215 | 0.00185 | 2.01E−07 | 1.004 |
| Long MisT | 9320.1 | 0.00131 | 1.41E−07 | 0.703 |
| Long MisA | 9329.1 | 0.00127 | 1.36E−07 | 0.681 |
| Long MisC | 9305.1 | 0.00126 | 1.35E−07 | 0.677 |
| Long compliment | 9345.1 | 0.00131 | 1.4E−07 | 0.701 |
| Capture probe short | 3420.5 | 0.00055 | 1.61E−07 | 0.804 |
| Short nonsense | 3052 | 0.00037 | 1.21E−07 | 0.606 |
| Short MisT | 3092.1 | 0.00041 | 1.33E−07 | 0.663 |
| Short MisA | 3101.1 | 0.00043 | 1.39E−07 | 0.693 |

TABLE 1

Oligonucleotides containing SNPs within the plant polynucleotide, MZA11874-27-Q1 marker.

| Crop | Sequence | SNP_NAME | MARKER_NAME | SNP_ID |
|---|---|---|---|---|
| Zea mays | ATCT(C)CTGCC (SEQ ID NO: 1 // short capture probe) | MZA11874-27 | MZA11874-27-Q1 | MZA11874-27/MZA11874/252 |
| Zea mays | GGCAG(G)AGAT (SEQ ID NO: 2 // short compliment) | MZA11874-27 | MZA11874-27-Q1 | MZA11874-27/MZA11874/252 |
| Zea mays | GGCAG(C)AGAT (SEQ ID NO: 3 // short MisC) | MZA11874-27 | MZA11874-27-Q1 | MZA11874-27/MZA11874/252 |
| Zea mays | GGCAG(T)AGAT (SEQ ID NO: 4 // short MisT) | MZA11874-27 | MZA11874-27-Q1 | MZA11874-27/MZA11874/252 |
| Zea mays | GGCAG(A)AGAT (SEQ ID NO: 5 // short MisA) | MZA11874-27 | MZA11874-27-Q1 | MZA11874-27/MZA11874/252 |
| Zea mays | TGGAC(A)TGAC (SEQ ID NO: 6 // short nonsense) | MZA11874-27 | MZA11874-27-Q1 | MZA11874-27/MZA11874/252 |
| Zea mays | CACCATCT(C)CTGCCC TTCTACGGAGTAGTT (SEQ ID NO: 7 // long capture probe) | MZA11874-27 | MZA11874-27-Q1 | MZA11874-27/MZA11874/252 |
| Zea mays | AACTACTCCGTAGAAG GGCAG(G)AGATGGTG (SEQ ID NO: 8 // long compliment) | MZA11874-27 | MZA11874-27-Q1 | MZA11874-27/MZA11874/252 |
| Zea mays | AACTACTCCGTAGAA GGGCAG(C)AGATGGTG (SEQ ID NO: 9 // MisC) | MZA11874-27 | MZA11874-27-Q1 | MZA11874-27/MZA11874/252 |
| Zea mays | AACTACTCCGTAGAA GGGCAG(T)AGATGGTG (SEQ ID NO: 10 // long MisT) | MZA11874-27 | MZA11874-27-Q1 | MZA11874-27/MZA11874/252 |
| Zea mays | AACTACTCCGTAGAA GGGCAG(A)AGATGGTG (SEQ ID NO: 11 // long MisA) | MZA11874-27 | MZA11874-27-Q1 | MZA11874-27/MZA11874/252 |
| Zea mays | AGCAATTGCATACACG GTCTG(G)ACATGCTA (SEQ ID NO: 12 // long nonsense) | MZA11874-27 | MZA11874-27-Q1 | MZA11874-27/MZA11874/252 |

TABLE 2-continued

| ID | MW (g/mol) | g | mol | ml to add for 200 µM |
|---|---|---|---|---|
| Short MisC | 3077.1 | 0.00045 | 1.46E−07 | 0.731 |
| Short compliment | 3117.1 | 0.0004 | 1.28E−07 | 0.642 |

The oligonucleotides represent SNP obtained from a plant genomic sequence. These SNP sequences were analyzed using SPR according to the following conditions.

Example 2: Detection of SNPs from Plant Polynucleotides Using SPR

The SPR experiments and analysis were completed using a Biacore 8K with the Insight software package (Cytiva™). First an SA (Cytiva™) sensor chip was prepared on the Biacore 8K (Cytiva™). The Running buffer that was used for the assay was 1×HBS-EP+ (Cytiva™). Flow cell 2 active cell, flow cell 1 inactive (no capture probe). Next, the sensor chip was washed three times with 50 mM NaOH+1M NaCl. The SPR assay was performed with a capture of the short probe on channels 1-4 and the long probe on channels 5-8, by flowing a 50 µM solution of each probe over the assigned channel at 10 µL/min for 60 seconds. For the short probe channels 1-4~1100 RU was captured. For the long probe channels 5-8~2100 RU was captured. Single cycle kinetics (SCK) were used to test assay results. Table 3 describes the method parameters used for the SPR assay.

TABLE 3

| Method Condition | Unit of Measurement |
|---|---|
| Contact time (association): | 120 seconds |
| Dissociation: | 300 seconds |
| Rate: | 30 µL/min |
| Buffer: | 1X HBS-EP+ |
| Cycle 1: | Blank cycle (buffer only) on each channel |
| Cycle 2: | Log-scale dilutions of each primer; 0.001, 0.01, 0.1, 1 and 10 µM. |
| Regeneration: | 50 mM NaOH |
| Total run time: | 50 minutes |

Two plates were assayed. The first plate contained the following samples, where the various probes were aliquoted into the following channels. Channel 1 included SEQ ID NO:2 (short compliment). Channel 2 included SEQ ID NO:3 (short MisC). Channel 3 include SEQ ID NO:4 (short MisT). Channel 4 include SEQ ID NO:6 (short nonsense). Channel 5 included SEQ ID NO:8 (long compliment). Channel 6 include SEQ ID NO:9 (long MisC). Channel 7 included SEQ ID NO: 10 (long MisT). Chanel 8 included SEQ ID NO:12 (long nonsense). The second plate contained the following samples, where the various probes were aliquoted into the following channels. Channel 1 included SEQ ID NO:8 (long compliment). Channel 2 included SEQ ID NO:5 (short misA). Channel 3 included SEQ ID NO:10 (long MisT). Channel 4 included SEQ ID NO: 12 (long nonsense). Channel 5 included SEQ ID NO:2 (short compliment). Channel 6 included SEQ ID NO: 5 (long MisA). Channel 7 included SEQ ID NO:4 (short MisT). Channel 8 included SEQ ID NO: 6 (short nonsense). The plates containing the plant polynucleotides that contained various types of SNPs within a marker were assayed using SPR according to these conditions.

Example 3: SPR Detection of SNPs from Plant Polynucleotides

The results from the SPR assay were obtained and are provided in the following sensograms. The sensograms of the reference substracted data and curve fitting resulted in distinct profiles for each of the SNPs that were assayed. In these sensograms the light grey line provides the actual data of the SNP that was assayed vis SPR and the black line provides the software fit. These results were fit to a 1:1 binding model; with the exception of the short probe-long compliment was fit to heterogeneous model. The sensograms depict the X-axis units: time in seconds and the Y axis units: Response Units (RU).

FIG. 1 provides the sensogram for the binding of the short probe (SEQ ID NO:1)::short compliment (SEQ ID NO:2). The alignment provided in FIG. 2 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 3:
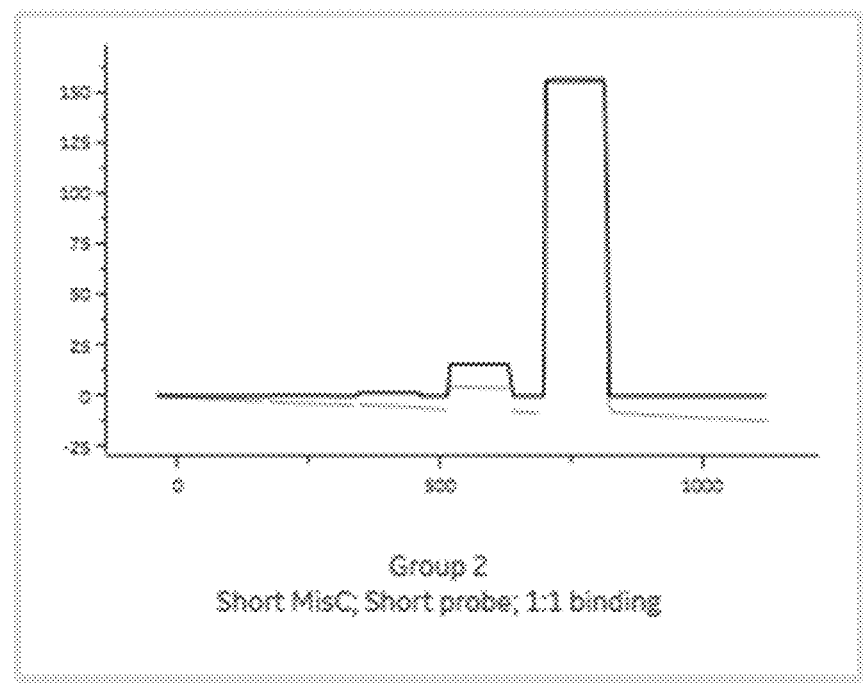
FIG. 3 provides the sensogram for the binding of the short probe (SEQ ID NO:1)::short MisC (SEQ ID NO:3).

FIG. 3 provides the sensogram for the binding of the short probe (SEQ ID NO:1)::short MisC (SEQ ID NO:3). The alignment provided in FIG. 4 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 5:
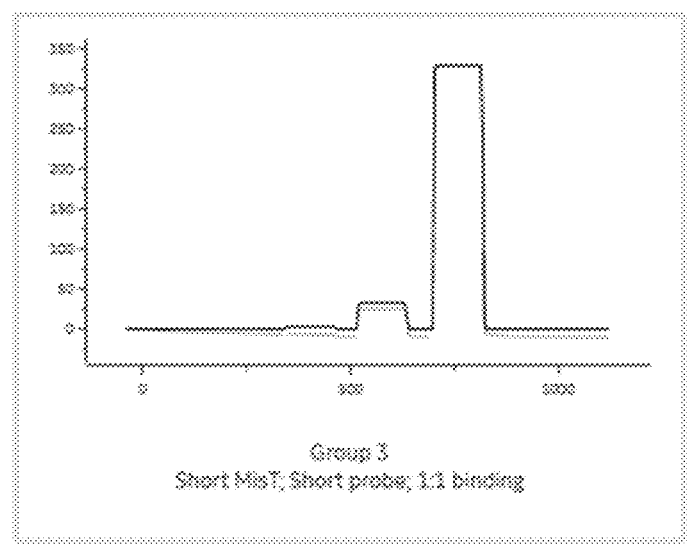
FIG. 5 provides the sensogram for the binding of the short probe (SEQ ID NO:1)::short MisT (SEQ ID NO:4).

FIG. 5 provides the sensogram for the binding of the short probe (SEQ ID NO:1)::short MisT (SEQ ID NO:4). The alignment provided in FIG. 6 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 7:
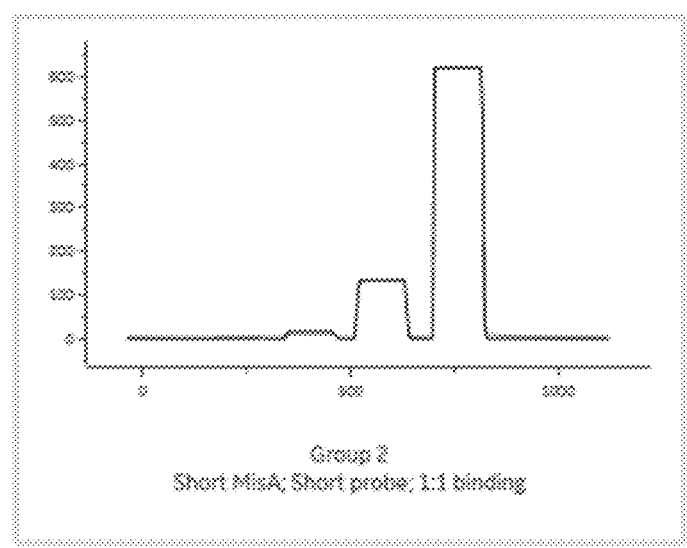
FIG. 7 provides the sensogram for the binding of the short probe (SEQ ID NO:1)::short MisA (SEQ ID NO:5).

FIG. 7 provides the sensogram for the binding of the short probe (SEQ ID NO:1)::short MisA (SEQ ID NO:5). The alignment provided in FIG. 8 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 9:
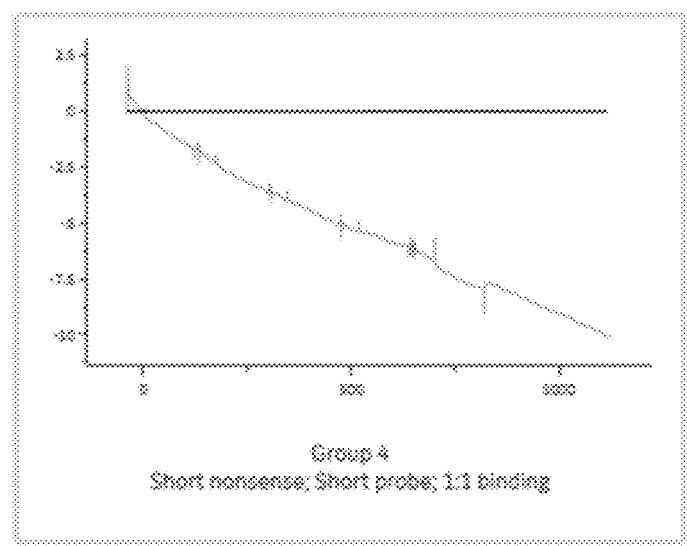
FIG. 9 provides the sensogram for the binding of the short probe (SEQ ID NO:1)::short nonsense (SEQ ID NO:6).

FIG. 9 provides the sensogram for the binding of the short probe (SEQ ID NO:1)::short nonsense (SEQ ID NO:6). The alignment provided in FIG. 10 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 11:
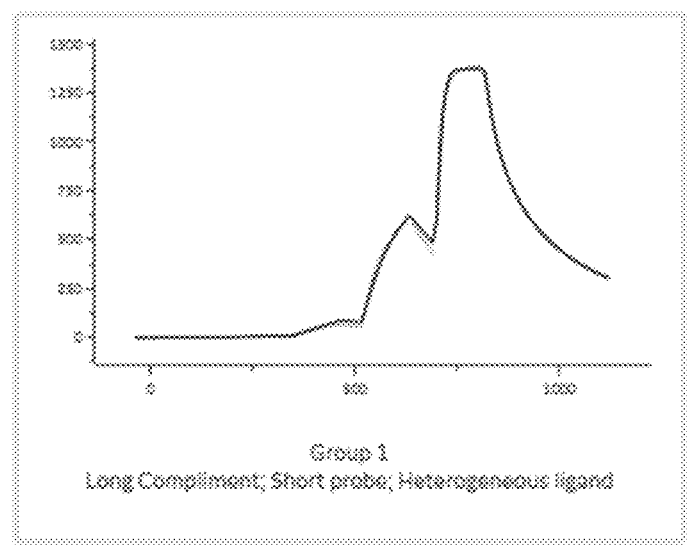
FIG. 11 provides the sensogram for the binding of the short probe (SEQ ID NO:1)::long compliment (SEQ ID NO:8).

FIG. 11 provides the sensogram for the binding of the short probe (SEQ ID NO:1)::long compliment (SEQ ID NO:8). The alignment provided in FIG. 12 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 13:
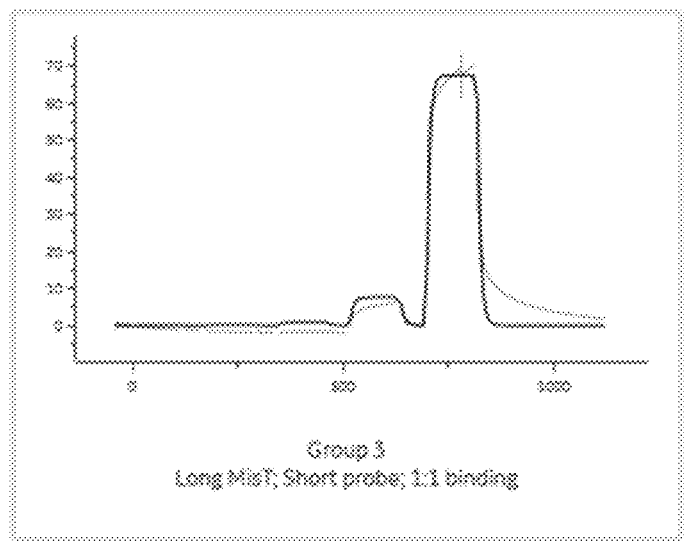
FIG. 13 provides the sensogram for the binding of the short probe (SEQ ID NO:1)::long MisT (SEQ ID NO:10).

FIG. 13 provides the sensogram for the binding of the short probe (SEQ ID NO:1)::long MisT (SEQ ID NO:10). The alignment provided in FIG. 14 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 15:
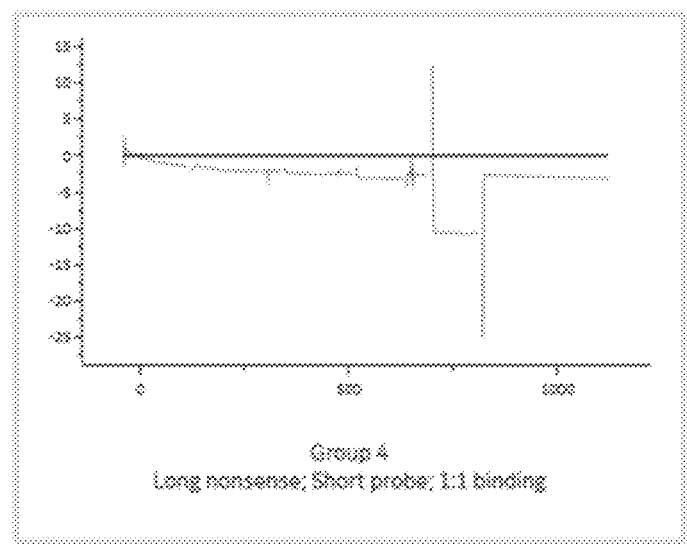
FIG. 15 provides the sensogram for the binding of the short probe (SEQ ID NO:1)::long nonsense (SEQ ID NO:11).

FIG. 15 provides the sensogram for the binding of the short probe (SEQ ID NO:1)::long nonsense (SEQ ID NO:11). The alignment provided in FIG. 16 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 17:
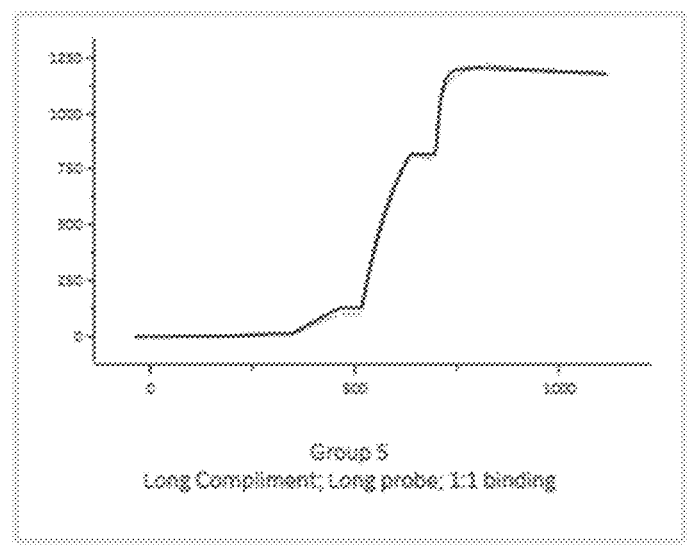
FIG. 17 provides the sensogram for the binding of the long probe (SEQ ID NO:7)::long compliment (SEQ ID NO:8).

FIG. 17 provides the sensogram for the binding of the long probe (SEQ ID NO:7)::long compliment (SEQ ID NO:8). The alignment provided in FIG. 18 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 19:
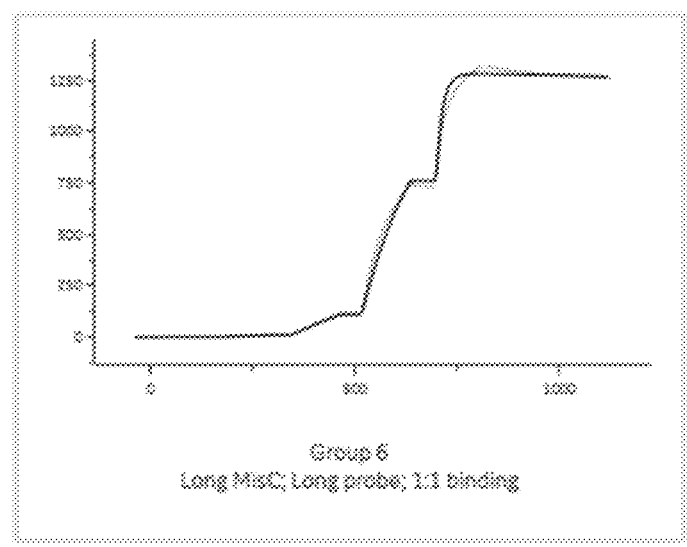
FIG. 19 provides the sensogram for the binding of the long probe (SEQ ID NO:7)::long MisC (SEQ ID NO:9).

FIG. 19 provides the sensogram for the binding of the long probe (SEQ ID NO:7)::long MisC (SEQ ID NO:9). The alignment provided in FIG. 20 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 21:
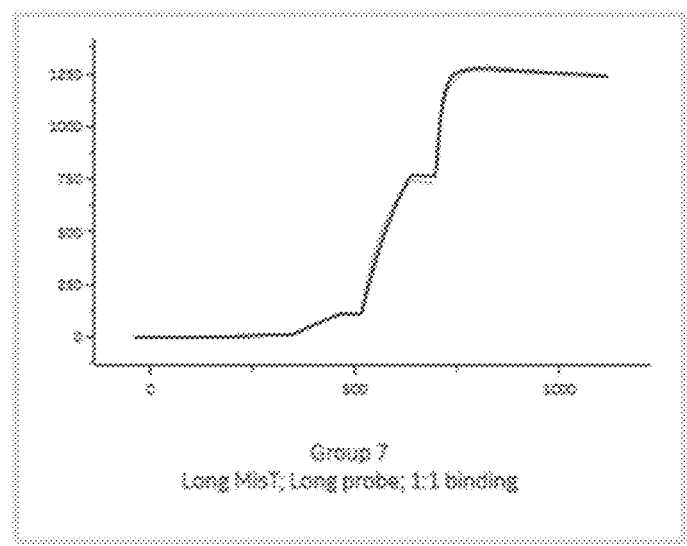
FIG. 21 provides the sensogram for the binding of the long probe (SEQ ID NO:7)::long MisT (SEQ ID NO:10).

FIG. 21 provides the sensogram for the binding of the long probe (SEQ ID NO:7)::long MisT (SEQ ID NO:10). The alignment provided in FIG. 22 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 23:
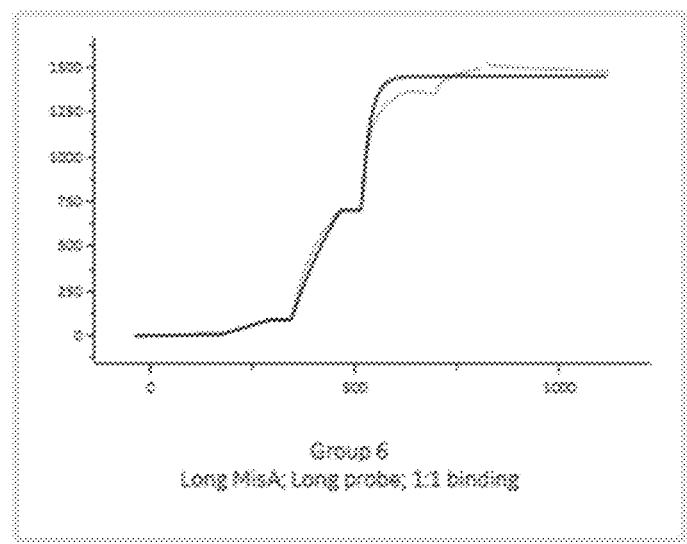
FIG. 23 provides the sensogram for the binding of the long probe (SEQ ID NO:7)::long MisA (SEQ ID NO:11).

FIG. 23 provides the sensogram for the binding of the long probe (SEQ ID NO:7)::long MisA (SEQ ID NO:11). The alignment provided in FIG. 24 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 25:
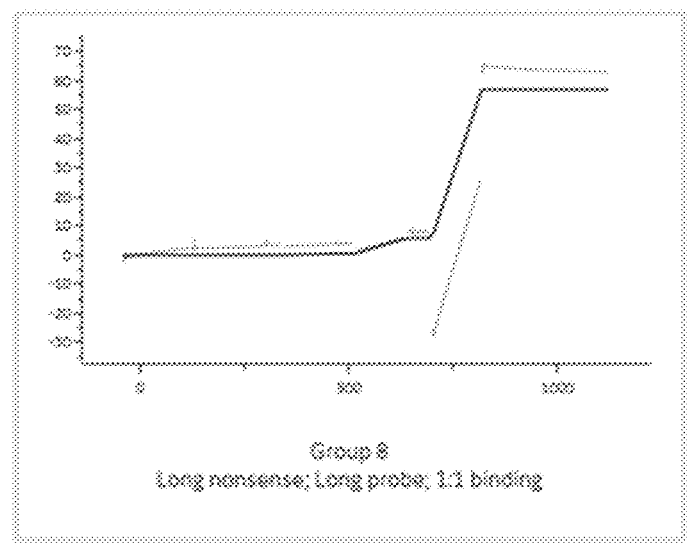
FIG. 25 provides the sensogram for the binding of the long probe (SEQ ID NO:7)::long nonsense (SEQ ID NO:12).

FIG. 25 provides the sensogram for the binding of the long probe (SEQ ID NO:7)::long nonsense (SEQ ID NO:12). The alignment provided in FIG. 26 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 27:
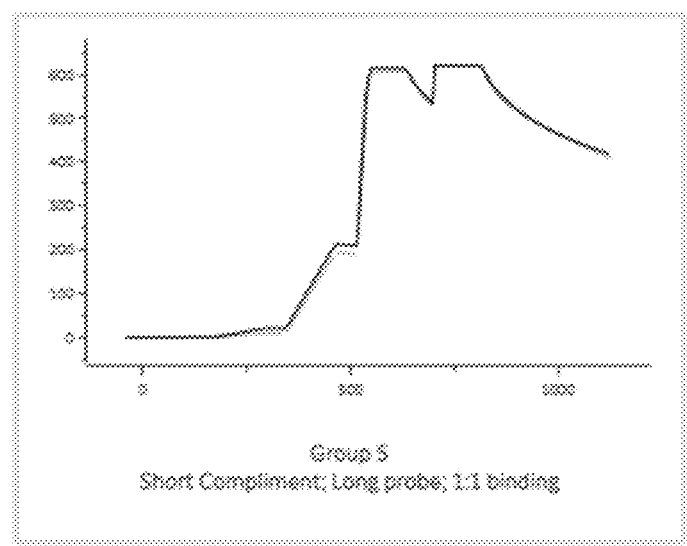
FIG. 27 provides the sensogram for the binding of the long probe (SEQ ID NO:7)::short compliment (SEQ ID NO:2).

FIG. 27 provides the sensogram for the binding of the long probe (SEQ ID NO:7)::short compliment (SEQ ID NO:2). The alignment provided in FIG. 28 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 29:
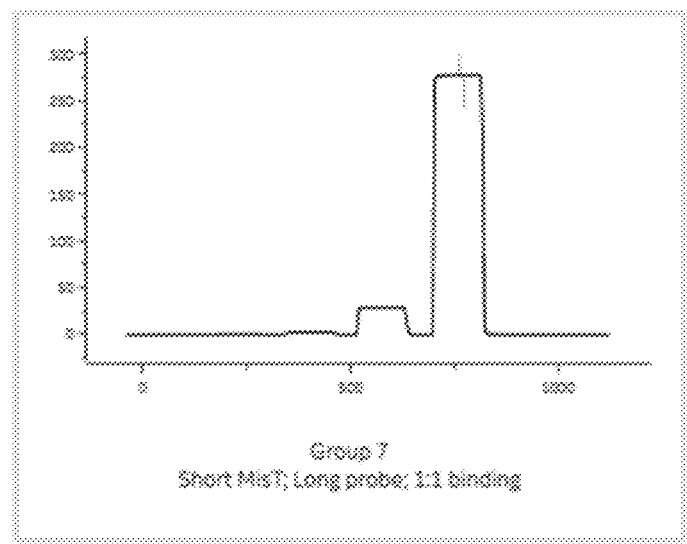
FIG. 29 provides the sensogram for the binding of the long probe (SEQ ID NO:7)::short MisT (SEQ ID NO:4).

FIG. 29 provides the sensogram for the binding of the long probe (SEQ ID NO:7)::short MisT (SEQ ID NO:4). The alignment provided in FIG. 30 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

Figure 31:
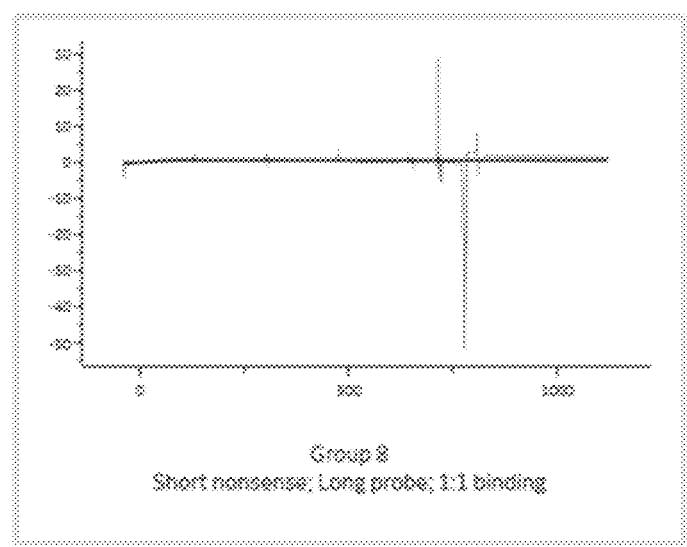
FIG. 31 provides the sensogram for the binding of the long probe (SEQ ID NO:7)::short nonsense (SEQ ID NO:6).

FIG. 31 provides the sensogram for the binding of the long probe (SEQ ID NO:7)::short nonsense (SEQ ID NO:6). The alignment provided in FIG. 32 illustrates how the oligonucleotide sequences hybridized to one another. As can be identified in this sequence alignment there is a SNP that is not complimentary and is annotated in brackets. The sensogram resulting from the SPR assay can be utilized to detect this specific SNP.

These sensograms indicate that a single nucleotide difference, which relates to an SNP, can be detected with a unique signature via SPR. Differing lengths of oligonucleotides result in unique SPR signatures. Accordingly, the SPR method can be utilized to detect SNPs from polynucleotides produced from plant genomic DNA. Once the SPR detection signatures are identified this assay can be utilized in various genotyping and sequencing applications for improved plant breeding.

Example 4: SPR Assays for Plant Breeding: Sequence Directed Selection

The SPR assay can be used for detection of the incorporation of important traits into progeny plants produced from parental crossing. SNP markers or unique polynucleotide sequences can be identified that are linked in close proximity to the important traits from the parental lines. The types of important traits, but are not limited to, transgenes, disease resistance, pest resistance, quality traits, agronomic traits, etc. Once a breeder has this knowledge they can utilize the SNP or unique polynucleotide sequences associated with the marker, and screen progeny for these SNPs or unique polynucleotide sequences that are linked with a target trait.

More specifically, a marker containing a SNP identified with a target trait can be identified in *Zea mays*. One with skill in the art would be able to develop oligonucleotides that recognize the marker. These oligonucleotides can be used to screen polynucleotide fragments from the genome of *Zea mays* utilizing the SPR assay as described herein. Upon reviewing the SPR assay sensograms, one with skill in the art can identify specific progeny plants that contain the desired SNP and select such plants.

Likewise, a marker containing a SNP identified with a target trait can be identified in *Glycine max*. One with skill in the art would be able to develop oligonucleotides that recognize the marker. These oligonucleotides can be used to screen polynucleotide fragments from the genome of *Glycine max* utilizing the SPR assay as described herein. Upon reviewing the SPR assay sensograms, one with skill in the art can identify specific progeny plants that contain the desired SNP and select such plants.

Example 5: SPR Assays for Plant Breeding: Sequence Directed Introgression

The SPR assay can be used for common methodologies in plant breeding such as backcrossing. Backcrossing allows a breeder to extract one or more of the best characteristics in a donor line and systematically introgress them into a recurrent parent line. In essence, the genomic region(s) at one or more selected donor DNA loci are systematically introgressed into a recurrent parent genome, replacing the nucleic acids at the corresponding loci in the recurrent parent genome. The types of characteristics that are typically introgressed between lines include, but are not limited too, transgenes, disease resistance, pest resistance, quality traits, agronomic traits, etc. Traditionally, this process can take five or more generations to obtain the traits of interest in a progeny that also shows equivalency to the recurrent parent and has the recurrent parent's agronomic performance. If the performance of the converted line does not equal the predicted performance of the recurrent parent plus the new trait, it can often be very difficult to understand the issue and how to correct.

Incorporating the ability to determine a polynucleotide sequence from a plant genome for use in Sequence Directed Back-Crossing (SDBC) can greatly accelerate the process by reducing the number of generations and result in a more quantifiable outcome. Using sequences, the progeny from each back-cross generation are examined for both the nucleic acid sequences of the donor parent that encode or are linked to the characteristics of interest and nucleic sequences in the recurrent parent genome. The examination takes into account both differences (polymorphisms) and identity between the sequences. Back-cross progeny are selected and advanced based on their nucleic acid sequence composition, which includes both the nucleic acid sequences encoding or linked to the target trait and the highest percent of nucleic acid sequences matching the recurrent parent sequence. By directing the process using SPR sequence rather than PCR, the process can be completed more quickly, possibly with a higher recovery of the recurrent parent.

The methods of the subject disclosure can be applied to SDBC. Specific sequences that are associated with a target trait can be readily screened by the SPR assay. More specifically, an SNP from a polynucleotide identified with a target trait can be identified in a plant (for example, *Zea mays* or *Glycine max*). One with skill in the art would be able to develop oligonucleotides that recognize the marker. These oligonucleotides can be used to screen polynucleotide fragments from the genome of a plant (for example, *Zea mays* or *Glycine max*) utilizing the SPR assay as described herein. Upon reviewing the SPR assay sensograms, one with skill in the art can identify specific progeny plants that contain the desired SNP and select such plants.

Example 6: SPR Assays for Plant Breeding: Molecular Fingerprinting

Molecular fingerprints based on nucleotide profiles may provide general information across the genome that can be used, among other applications, to assess germplasm diversity, to help the selection of high performing parents and testers, to query new germplasm pools for potential introgression targets, to query new or existing germplasm pools for genomic regions associated with at least one phenotype of interest. If two lines are sufficiently diverse, they are likely in different heterotic groups. That is, they can complement each other, and, when hybridized, have a high probability of generating a productive breeding cross or a hybrid combination. On the other hand, similarity among lines may suggest a potential suboptimal cross in hybrid plants like corn.

Molecular fingerprints may focus on selected regions of the genome and reveal sequence information at specific loci including, but not limited to, those that are causative or linked to traits of economical importance. The presence or absence of particular nucleotide sequences or particular nucleotide sequence variants at one or more loci can be associated with the traits of interests, and used to predict the performance of these traits, and to select high performing lines in lieu of direct phenotyping. Molecular fingerprints can be generated based on whole genome sequences, which is costly and time consuming, and often times not practical. The genome complexity could be reduced using various methods before sequencing to produce fingerprints that are based on a small representation (selected regions or loci) of the genome. The present invention provides a more efficient and cost effective approach than the current art.

For molecular fingerprinting, the first step is to select the polymorphic regions or loci to be used to generate the nucleotide sequence-based molecular fingerprints. SNPs are one source of candidate loci although they are not the only source. The number of loci used is determined by many factors including, but not limited to, the objectives and budgets of the projects as well as the structure of the genomes under investigation.

The SPR assay can be used for molecular fingerprinting of plants. The methods of the subject disclosure can be applied to molecular fingerprinting. Specific sequences that are associated with a target trait can be readily screened by the SPR assay. More specifically, an SNP from a polynucleotide identified with a target trait can be identified in plants (for example, *Zea mays* or *Glycine max*). One with skill in the art would be able to develop oligonucleotides that recognize the marker. These oligonucleotides can be used to screen polynucleotide fragments from the genome of plants (for example, *Zea mays* or *Glycine max*) utilizing the SPR assay as described herein. Upon reviewing the SPR assay sensograms, one with skill in the art can identify specific progeny plants that contain the desired SNP and select such plants.

Example 7: SPR Assays for Plant Breeding: Mining Rare Alleles

The SPR assay can be used to detect rare alleles or haplotypes in the genome of a plant. The ability to identify rare alleles or haplotypes allows for plant breeders to introgress these regions from parental plants into progeny plants. Those having skill in the art can identify SNPs associated with the rare allele in one parent and then apply the SPR assay to detect the rare allele in the progeny plants. This is particularly important for leveraging rare but important genomic regions in a breeding program, such as a disease resistance locus from exotic or unadapted germplasm pool. The present example provides methods for rare allele detection, experimental design (i.e., selecting exotic germplasm, germplasm with known phenotype of interest, screening non-elite gp), and utility (i.e., introgression programs for beneficial rare variants for specific traits and/or to expand germplasm diversity in one or more specific germplasm pools such as per maturity zone).

Using the methods and compositions of the subject disclosure an SPR assay can be used to detect a polynucleotide obtained from a plant genomic sequence. Using methods known in the art for sequence alignment and in silico evaluation, differences and similarities are identified and linked to the source germplasm entry. Following identification of alleles of interest, selection decisions can be made.

Example 8: SPR Assays for Plant Breeding: Detection of SNPs from Chloroplast and Mitochondrial DNA SPR is used to detect the presence of SNPs directly from chloroplast or mitochondrial DNA isolated from a plant tissue. Tissues, organs, seeds and other types of plant material can serve as a source for the isolation of chloroplast or mitochondrial DNA using known chloroplast or mitochondrial DNA isolation methodology. Once the chloroplast or mitochondrial DNA is isolated, the methods outlined in Table 3 provide exemplary conditions for completing the SPR assay on the chloroplast or mitochondrial DNA. Those with skill in the art would appreciate that the chloroplast or mitochondrial DNA possesses a large number of polynucleotides and that modifications to the conditions in Table 3 are necessary to complete the SPR assay. Accordingly, further method optimization may need to occur with this new sample type, by changing variables within Table 3. The chloroplast or mitochondrial DNA is prepared in a manner to optimize binding to the single stranded probe attached to the SPR chip. Based on the sensogram profiles generated within, the shape and quality of the plotted data indicates the presence (or absence) of the SNP of interest. Using the methods and compositions of the subject disclosure an SPR assay can be used to detect a polynucleotide obtained from a plant chloroplast or mitochondrial material. The identification of SNPs in the plant chloroplast or mitochondrial DNA can be used to select plant material for breeding applications.

Example 9: SPR Assays for Plant Breeding: Detection of SNPs from Genomic DNA

SPR is used to detect the presence of SNPs directly from genomic DNA isolated from a plant tissue. Tissues, organs, seeds and other types of plant material can serve as a source for the isolation of genomic DNA using known genomic DNA isolation methodology. Once the genomic DNA is isolated, the methods outlined in Table 3 provide exemplary conditions for completing the SPR assay on the genomic DNA. Those with skill in the art would appreciate that the genomic DNA possesses a large number of polynucleotides and that modifications to the conditions in Table 3 are necessary to complete the SPR assay. Accordingly, further method optimization may need to occur with this new sample type, by changing variables within Table 3. The genomic DNA is prepared in a manner to optimize binding to the single stranded probe attached to the SPR chip. Based on the sensogram profiles generated within, the shape and quality of the plotted data indicates the presence (or absence) of the SNP of interest. Using the methods and compositions of the subject disclosure an SPR assay can be used to detect a polynucleotide obtained from a plant genomic material. The identification of SNPs in the plant genomic DNA can be used to select plant material for breeding applications.

In the case of rare allele mining, the rare allele may be associated with a known phenotype. In addition, the identification of the rare allele can provide the basis for additional phenotyping, association studies, and other assays to evaluate the effect of the rare allele on plant phenotype and breeding performance. Further, the direct nucleic acid sequence of the rare allele can be immediately leveraged for use as a marker via methods known in the art and described herein to detect this rare allele in additional germplasm entries, to be used as a basis for selection, and to facilitate introgression of the rare allele in germplasm entries lacking the rare allele. In other aspects, the rare allele can be isolated and the isolated nucleic acid is transformed into a plant using methods known in the art in order to confer a preferred phenotype to the recipient plant. The recipient plant can subsequently be used as a donor for conversion programs to cross with elite germplasm for trait integration purposes.

The identification of rare alleles is useful for leveraging the full genetic potential of any germplasm pool. This is useful for determining breeding cross strategy, increasing the diversity between germplasm pools, evaluating heterotic pools, and informing breeding decisions. High throughput analysis of the germplasm pool via an SPR method of the subject disclosure both accelerates the identification of the alleles and allows simultaneous detection of rare alleles and identification of associated SNPs which could be used to develop new marker.

While the present disclosure may be susceptible to various modifications and alternative forms, specific embodiments have been described by way of example in detail herein. However, it should be understood that the present disclosure is not intended to be limited to the particular forms disclosed. Instead, the present disclosure is to cover all modifications, equivalents, and alternatives falling within the scope of the present disclosure as defined by the following appended claims and their legal equivalents.

What is claimed is:

1. A method for genotyping a plant polynucleotide for the presence or absence of a Single Nucleotide Polymorphism (SNP) using a Surface Plasmon Resonance (SPR) assay, the method comprising the following steps:
   a. Providing an oligonucleotide probe;
   b. Providing a plant polynucleotide, wherein the oligonucleotide probe and plant polynucleotide are fully complementary to one another;
   c. Hybridizing the oligonucleotide probe with the plant polynucleotide;
   d. Complexing the oligonucleotide probe and plant polynucleotide to an SPR biosensor chip;
   e. Quantitating the hybridization of the oligonucleotide probe with the plant polynucleotide to determine the affinity of oligonucleotide probe to the plant polynucleotide; and
   f. Determining that the plant polynucleotide contains the presence or absence of an SNP.

2. The method of claim 1, the method further comprising the step of:
   a. Denaturing the oligonucleotide probe and plant polynucleotide to a single stranded oligonucleotide probe and a single stranded plant polynucleotide;
   b. Hybridizing the single stranded oligonucleotide probe with the single stranded plant polynucleotide, wherein the single stranded probe and the single stranded polynucleotide are fully complementary to one another;
   c. Complexing the hybridized oligonucleotide probe and plant polynucleotide to an SPR biosensor chip; and
   d. Linking the hybridized oligonucleotide probe and plant polynucleotide to the surface of metal film on a glass chip and immobilizing the hybridized oligonucleotide probe and plant polynucleotide.

3. The method of claim 1, the method further comprising the step of:
   a. Denaturing the oligonucleotide probe and plant polynucleotide to a single stranded oligonucleotide probe and a single stranded plant polynucleotide;
   b. Complexing the single stranded oligonucleotide probe to an SPR biosensor chip;
   c. Linking the single stranded oligonucleotide probe to the surface of metal film on a glass chip and immobilizing the single stranded oligonucleotide probe; and
   d. Hybridizing the single stranded oligonucleotide probe linked to the glass chip with the single stranded plant polynucleotide, wherein the single stranded oligonucleotide probe and the single stranded plant polynucleotide are fully complementary to one another.

4. The method of claim 1, the method further comprising the step of:
   a. Denaturing the oligonucleotide probe and plant polynucleotide to a single stranded oligonucleotide probe and a single stranded plant polynucleotide;
   b. Complexing the single stranded plant polynucleotide to an SPR biosensor chip;
   c. Linking the single stranded plant polynucleotide to the surface of metal film on a glass chip and immobilizing the single stranded plant polynucleotide; and
   d. Hybridizing the single stranded plant polynucleotide linked to the glass chip with the single stranded oligonucleotide probe, wherein the single stranded plant polynucleotide and single stranded oligonucleotide probe are fully complementary to one another.

5. The method as in one of claim 2, 3 or 4, wherein the metal is copper, silver, aluminum or gold.

6. The method of claim 1, wherein the probe comprises a plant genomic marker.

7. The method of claim 6, wherein the probe comprises an SNP.

8. The method of claim 1, wherein the plant polynucleotide comprises a plant genomic marker.

9. The method of claim 8, wherein the plant genomic marker comprises an SNP.

10. The method of claim 1, wherein the plant polynucleotide is selected from the group consisting of genomic DNA, cDNA, bacterial artificial chromosome, yeast artificial chromosome, whole genome amplified DNA, and PCR product.

11. The method of claim 10, wherein the plant polynucleotide is restricted with at least one restriction endonuclease.

12. The method of claim 11, wherein the restriction endonuclease is a rare cutter.

13. The method of claim 11, wherein the restriction endonuclease is a frequent cutter.

14. The method of claim 1, wherein the SNP is either an A, C, T, or G.

15. The method of claim 1, wherein the SNP is indicative of an economically important trait in a plant and wherein said economically important trait is selected from the group consisting of herbicide tolerance, disease resistance, insect or pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility.

16. The method of claim 1, wherein the SNP is indicative of an insertion or deletion within a DNA sequence (INDEL), simple sequence repeats of DNA sequence (SSRs), a restriction fragment length polymorphism (RFLP), and a variation in copy number.

17. The method of claim 1, wherein the SNP is indicative of a transgene.

18. The method of claim 1, wherein the genotyping is used for applications selected from the group consisting of genetic mapping, quantitative trait loci mapping, fine mapping genes/traits, linkage disequilibrium mapping, marker-assisted back-crossing, genetic distance analysis, discovery of markers linked to traits or phenotypes, and diagnostic genotyping of plant samples.

19. The method of claim 1, further comprising (a) producing multiple libraries from multiple plant polynucleotide samples and (b) pooling the libraries prior to the SPR assay.

\* \* \* \* \*

SEQUENCE LISTING

<160> NUMBER OF SEQ ID NOS: 12

<210> SEQ ID NO 1
<211> LENGTH: 9
<212> TYPE: DNA
<213> ORGANISM: Zea mays

<400> SEQUENCE: 1 atctctgcc                                                         9

<210> SEQ ID NO 2
<211> LENGTH: 10
<212> TYPE: DNA
<213> ORGANISM: Zea mays

<400> SEQUENCE: 2
tagaggacgg                                                        10

<210> SEQ ID NO 3
<211> LENGTH: 10
<212> TYPE: DNA
<213> ORGANISM: Zea mays

```
<400> SEQUENCE: 3
tagacgacgg                                                                        10

<210> SEQ ID NO 4
<211> LENGTH: 10
<212> TYPE: DNA
<213> ORGANISM: Zea mays

<400> SEQUENCE: 4
tagatgacgg                                                                        10

<210> SEQ ID NO 5
<211> LENGTH: 10
<212> TYPE: DNA
<213> ORGANISM: Zea mays

<400> SEQUENCE: 5
tagaagacgg                                                                        10

<210> SEQ ID NO 6
<211> LENGTH: 10
<212> TYPE: DNA
<213> ORGANISM: Zea mays

<400> SEQUENCE: 6
cagtacaggt                                                                        10

<210> SEQ ID NO 7
<211> LENGTH: 30
<212> TYPE: DNA
<213> ORGANISM: Zea mays

<400> SEQUENCE: 7
caccatctcc tgcccttcta cggagtagtt                                                  30

<210> SEQ ID NO 8
<211> LENGTH: 30
<212> TYPE: DNA
<213> ORGANISM: Zea mays

<400> SEQUENCE: 8
gtggtagagg acgggaagat gcctcatcaa                                                  30

<210> SEQ ID NO 9
<211> LENGTH: 30
<212> TYPE: DNA
<213> ORGANISM: Zea mays

<400> SEQUENCE: 9
gtggtagacg acgggaagat gcctcatcaa                                                  30

<210> SEQ ID NO 10
<211> LENGTH: 30
<212> TYPE: DNA
<213> ORGANISM: Zea mays

<400> SEQUENCE: 10
gtggtagatg acgggaagat gcctcatcaa                                                  30

<210> SEQ ID NO 11
<211> LENGTH: 30
<212> TYPE: DNA
```

```
<213> ORGANISM: Zea mays

<400> SEQUENCE: 11
gtggtagaag acgggaagat gcctcatcaa                                      30

<210> SEQ ID NO 12
<211> LENGTH: 30
<212> TYPE: DNA
<213> ORGANISM: Zea mays

<400> SEQUENCE: 12
atcgtacagg tctggcacat acgttaacga                                      30
```